US009759723B2

(12) United States Patent
Sindhi et al.

(10) Patent No.: US 9,759,723 B2
(45) Date of Patent: *Sep. 12, 2017

(54) B-CELL ANTIGEN PRESENTING CELL ASSAY

(71) Applicant: University of Pittsburgh—Of the Commonwealth System of Higher Education, Pittsburgh, PA (US)

(72) Inventors: Rakesh Sindhi, Pittsburgh, PA (US); Chethan Ashokkumar, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/076,443

(22) Filed: Mar. 21, 2016

(65) Prior Publication Data

US 2016/0202258 A1    Jul. 14, 2016

Related U.S. Application Data

(63) Continuation of application No. 13/639,428, filed as application No. PCT/US2011/031705 on Apr. 8, 2011, now Pat. No. 9,322,827.

(60) Provisional application No. 61/322,234, filed on Apr. 8, 2010.

(51) Int. Cl.
| | |
|---|---|
| A61K 38/00 | (2006.01) |
| C12N 5/00 | (2006.01) |
| G01N 33/569 | (2006.01) |
| G01N 33/58 | (2006.01) |

(52) U.S. Cl.
CPC .  *G01N 33/56972* (2013.01); *G01N 33/56977* (2013.01); *G01N 33/582* (2013.01); *G01N 2333/70578* (2013.01); *G01N 2333/70596* (2013.01); *G01N 2800/245* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 5,061,620 A | 10/1991 | Tsukamoto et al. | |
| 2006/0275752 A1 | 12/2006 | Sindhi | |
| 2014/0057315 A1 | 2/2014 | Sindhi et al. | |

FOREIGN PATENT DOCUMENTS

WO    WO 2011/127360    10/2011

OTHER PUBLICATIONS

Ahmadi et al., "CD40 ligand-activated, antigen-specific B cells are comparable to mature dendritic cells in presenting protein antigens and major histocompatibility complex class I- and class II-binding peptides," *Immunology*, vol. 124(1): pp. 129-140, 2008.
Ashokkumar et al., "Allospecific CD154+ B cells associate with intestine allograft rejection in children," *Transplantation*, vol. 90(11): pp. 1226-1231, Dec. 15, 2010.
Ashokkumar et al., "Allospecific CD154+ T cells associate with rejection risk after pediatric liver transplantation," *Transplantation*, vol. 92, No. 4: pp. 433-438, Aug. 2011.
Ashokkumar et al., "Allospecific CD154+ T cells identify rejection-prone recipients after pediatric small-bowel transplantation," *Surgery*, vol. 146(2): pp. 166-173, Aug. 2009.
Ashokkumar et al., "Allospecific CD154+ T-cytotoxic memory cells identify recipients experiencing acute cellular rejection after renal transplantation," *American Journal of Transplantation*, vol. 9: pp. 179-191, 2009.
Ashokkumar et al., "Proliferative alloresponse of T cytotoxic cells identifies rejection-prone children with small bowel transplantation," *Transplantation*, vol. 89(11): pp. 1371-1377, Jun. 15, 2010.
Ashokkumar et al., "Proliferative alloresponse of T-cytotoxic cells identifies rejection-prone children with steroid-free liver transplantation," *Liver Transplantation*, vol. 15: pp. 978-985, Aug. 2009.
Bisikirska, et al., "TCR stimulation with modified anti-CD3 mAb expands CD8+ T cell population and induces CD8+ CD25+ Tregs." Journal of Clinical Investigation, 115.10: pp. 2904-2913, (2005).
Gupta et al., "Elevated myeloid: Plasmacytoid dendritic cell ratio associates with late, but not early, liver rejection in children induced with rabbit anti-human thymocyte globulin," *Transplantation*, vol. 88: pp. 589-594, Aug. 27, 2009.
Gupta, et al., "Elevated myeloid: plasmacytoid dendritic cell ratio associates with late, but not early liver rejection in children induced with, anti-human thymocyte globulin1," Transplantation, 88.4: 589-594 (2009).
Iacomini, et al., "Measuring T cell alloreactivity to predict kidney transplant outcomes: Are we there yet?" Journal of the American Society of Nephrology, 17.2: pp. 328-330, (2006).
International Search Report and Written Opinion by the Australian Patent Office for corresponding PCT Patent Application No. PCT/US2011/031705, 9 pp., issued Aug. 15, 2011.
Kirk et al., "The role of CD154 in organ transplant rejection and acceptance," *Phil. Tran. R Soc. Lond B*, vol. 356: pp. 691-702, 2001.
Parsons et al., "B-cell tolerance in transplantation: is repertoire remodeling the answer?" Expert Rev. *Clinical Immunology*, vol. 5(6): pp. 703-723, pp. 713-716, Nov. 2009.
Patent Examination Report No. 1 issued Jan. 15, 2014, by the Australian Intellectual Property Office, for corresponding Australian Patent Application No. 2011237393, filed Apr. 8, 2011, 4 pp.

(Continued)

*Primary Examiner* — Michail Belyavskyi
(74) *Attorney, Agent, or Firm* — Klarquist Sparkman, LLP

(57) ABSTRACT

Disclosed herein are methods for diagnosing or predicting B-cell rejection in a subject. In one example, for assessing transplant rejection, the method includes determining an antigen presenting index by comparing uptake of a donor antigen to uptake of a reference antigen in a biological sample obtained from the subject. In another example, for assessing GVHD, the method includes determining an antigen presenting index by comparing uptake of a recipient antigen to uptake of a reference antigen in a biological sample obtained from the subject.

22 Claims, 3 Drawing Sheets

(56) References Cited

OTHER PUBLICATIONS

Sindhi et al., "Allospecific CD154+ T-cytotoxic memory cells as potential surrogate for rejection risk in pediatric intestine transplantation," *Pediatric Transplantation*, vol. 16: pp. 83-91, 2012.

Sindhi et al., "Cellular alloresponses for rejection-risk assessment after pediatric transplantation," *Current Opinion in Organ Transplantation*, vol. 15: p. 515-521, 2011.

Sindhi et al., "Immune monitoring in small bowel transplantation," *Current Opinion in Organ Transplantation*, vol. 15: pp. 349-356, 2010.

Zharkin et al., "Characterization of intra-graft B cells during renal allograft rejection," *Kidney Int.*, vol. 74(5): pp. 664-673, Sep. 2008.

FIG. 3
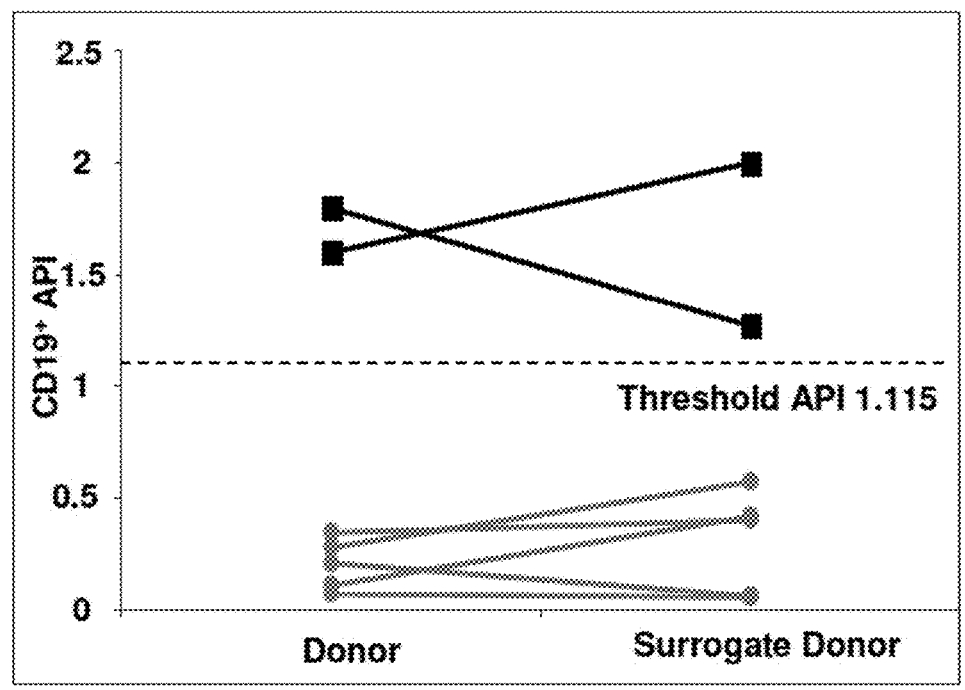
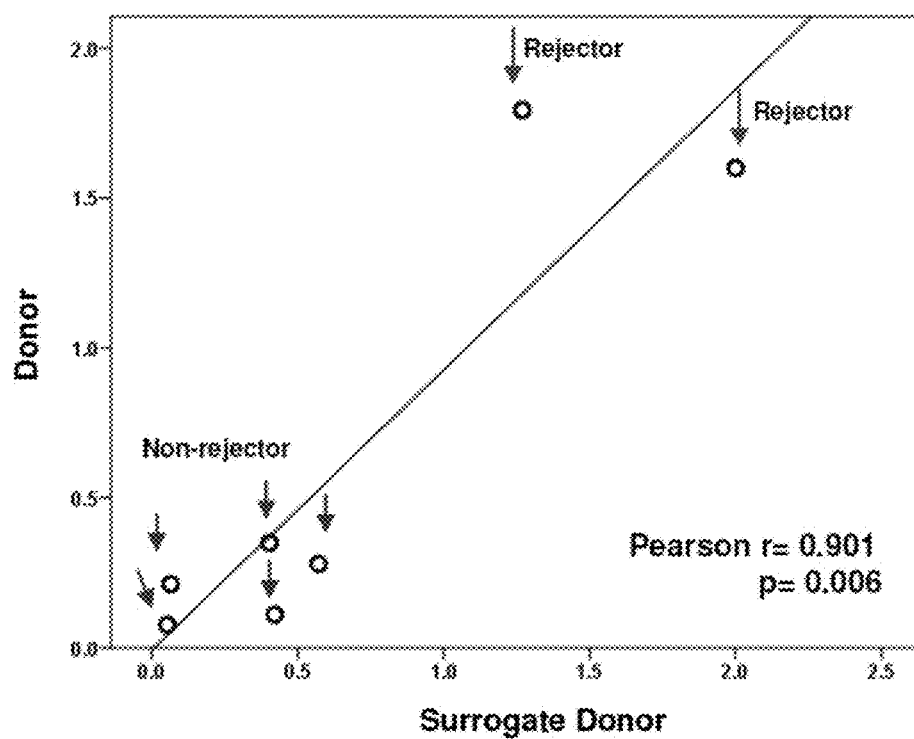

B-CELL ANTIGEN PRESENTING CELL ASSAY

CROSS REFERENCE TO RELATED APPLICATION

This is a continuation of U.S. patent application Ser. No. 13/639,428, filed Oct. 4, 2012, which is the U.S. National Stage of International Application No. PCT/US2011/031705, filed Apr. 8, 2011, which was published in English under PCT Article 21(2), which in turn claims the benefit of U.S. Provisional Application No. 61/322,234, filed Apr. 8, 2010. The prior applications are incorporated herein by reference in their entirety.

ACKNOWLEDGMENT OF GOVERNMENT SUPPORT

This invention was made with government support under Grant No. AI073895 awarded by the National Institutes of Health. The government has certain rights in this invention.

FIELD OF THE DISCLOSURE

This disclosure relates to the field of immunology and in particular, to methods for diagnosing and/or predicting transplant rejection, such as the acute cellular rejection or antibody-mediated (humoral) rejection of an organ transplant or graft-versus-host disease.

BACKGROUND

Transplanted organs and tissues are vulnerable to rejection; acute cellular rejection (ACR) and humoral rejection (HR) are two forms of transplant rejection. Either process begins with uptake of a foreign antigen by an antigen presenting cell (APC). An APC presents the antigen to effector cells, such as T- and B-lymphocytes. The way in which APCs present the antigen to the effector cells determines whether the immune system reacts with an inflammatory response, or is tolerized to the antigen. The inflammatory response to a transplanted organ is called alloresponse. An effector T-cell inflammatory alloresponse mediates ACR, while an effector B-cell inflammatory alloresponse includes maturation to antibody secreting memory B-cells (also known as plasma cells) which mediate HR.

In order to identify patients at high risk for rejecting a transplant, cardiac/organ transplantation candidates are prospectively tested for anti-HLA antibodies against lymphocytes from a panel of subjects representative of the major HLA allotypes, collectively referred to as measurements of panel-reactive antibodies (PRA). In addition to predicting an increased likelihood of donor-specific anti-HLA antibodies and a consequent risk of early graft failure related to humoral rejection, several studies have shown that high levels of pretransplant PRA in allograft recipients are associated with adverse post-transplant outcome when compared to patients with low or negative reactivity. High PRA levels have been associated, in some studies, with increased frequency of acute cellular rejection, decreased long-term graft survival, and increased mortality. Moreover, the onset of accelerated coronary artery disease (CAD) in cardiac transplant recipients, the major limitation to long-term graft survival, has been associated with the presence of anti-HLA antibodies. Since accelerated CAD in these patients may be a consequence of cumulative episodes of high-grade cellular rejections, it is possible that this association may actually reflect a relationship between anti-HLA antibodies and acute cellular rejection. However, PRA, and other test are not highly sensitive or specific. Thus, a need remains for a sensitive and specific assay for acute cellular and humoral rejection.

SUMMARY OF THE DISCLOSURE

The B-cell arises from bone marrow progenitor cells, which progress through multiple stages such as the pro-, pre-, and transitional stages into the naive B-cell. The B-cell has many functions. It can serve as an antigen presenting cell, which activates T-cytotoxic cells toward effector function, can activate naive or memory Th1 cells, or evolves into long-lived memory cell and transforms into an antibody secreting plasma cell with T-cell help, and perpetuates antibody responses to autoantigens. Antigen is sensed by the B-cell via the B-cell receptor, or the immunoglobulin molecule.

Antigen recognition, uptake and presentation are early steps in the many functions fulfilled by the B-cell. The inventors have developed methods and assays to measure this antigen presenting function for the early detection of activity or severity for a variety of immunological diseases caused by foreign and other antigens. These antigens include but are not limited to transplanted organs and tissues and cells, infectious pathogens, allergens, autoantigens (antigens arising from self, which would normally not evoke an immune response) and tumor antigens.

As such, disclosed herein are methods and assays for the diagnosis and prediction of B-cell activity, such as acute cellular or humoral rejection. Monitoring antigen uptake and presentation by APCs is used to determine whether the effector cell response will result in ACR, HR, or an absence thereof. In several examples, the disclosed assay is used to diagnose or predict organ transplant rejection, graft-versus-host disease (GVHD) or immunity to an antigen. For example, the assay is used to diagnose or predict GVHD after solid organ, bone-marrow, stem cell transplantation or a combination thereof. In other examples, the assay is used to predict immunity to tumor antigens, autoantigens, pathogen antigens or a combination thereof.

Also provided is a method of assessing organ rejection including contacting a first sample that includes APCs obtained from a subject in need of or having received an organ transplant from a donor, with a donor antigen from the donor, under conditions sufficient to induce uptake of the donor antigen, and measuring the uptake of the donor antigen. The method also includes contacting a second sample that includes APCs obtained from the subject in need of or having received an organ transplant, with a third-party antigen under conditions sufficient to induce uptake of the third-party antigen, and measuring the uptake of the third party antigen. The ratio of uptake of the donor antigen in the first sample to uptake of the third-party antigen in the second sample is then determined. If donor antigen uptake exceeds third-party antigen uptake in the form a ratio greater than one than the subject has, or is likely to develop, organ rejection. In some embodiments, the APC preparation consists of peripheral blood leukocytes. In some particular embodiments, the APC preparation consists of B-cells.

Also disclosed herein is a method for assessing B-cell rejection in a subject by determining an antigen presenting index (API). The method includes comparing uptake by recipient APCs of a donor antigen to the uptake by recipient APCs of a third-party antigen. An API of greater than one predicts with a sensitivity of at least 90% and a specificity of at least 90% for an increased risk of acute cellular or humoral rejection, or the presence of acute cellular or humoral rejection.

Also provided is method of assessing GVHD in a subject. The method includes assessing GVHD by contacting a first sample that includes donor APCs obtained from a sample of donor bone marrow or stem cells before transplantation, or from the recipient who has received donor bone marrow or stem cells, with a recipient antigen from a subject having received a bone marrow transplant or a stem cell transplant the recipient, under conditions sufficient to induce uptake of the recipient antigen, and measuring the uptake of the recipient antigen. The method also includes contacting a second sample that includes donor APCs obtained from a sample of donor bone marrow or stem cells before transplantation, from the recipient who has received donor bone marrow or stem cells, with a third-party antigen under conditions sufficient to induce uptake of the third-party antigen, and measuring the uptake of the third party antigen. The ratio of uptake of the recipient antigen in the first sample to uptake of the third-party antigen in the second sample is then determined A ratio of greater than one indicates that the subject has, or is likely to develop, GVHD. In some embodiments, the APC preparation consists of peripheral blood leukocytes. In some examples, the APC preparation consists of a B-cell, such as a donor B-cell.

Further provided are methods for determining the B-cell response to other antigens, including antigens from allergens, infectious pathogens, tumors or associated with autoimmune disorders/diseases. Infectious pathogens include bacteria, fungi, protists, prions and/or viruses. These additional uses can be either alone or in addition to diagnosing or predicting organ transplant rejection.

The foregoing and other features of the disclosure will become more apparent from the following detailed description of several embodiments, which proceeds with reference to the accompanying figures.

BRIEF DESCRIPTION OF THE FIGURES

FIG. 3 is a set of graphs of the API of CD19+B-cells obtained using "actual" donor and "surrogate" donor peripheral blood leukocytes (PBL) plotted for 7 children with liver or intestine transplantation. Surrogate donor consists of peripheral blood leukocytes from healthy normal human subjects which are HLA-matched to the actual donor, and therefore resemble this actual donor Correlation between API obtained with either stimulator were highly significant for either recipient population (left panel). Assignment of rejector (R) or non-rejector (NR) status based on a rejection-risk threshold API of ≥1.115 was the same with either stimulator for either recipient population (right panel).

DETAILED DESCRIPTION OF SEVERAL EMBODIMENTS

Figure 1:
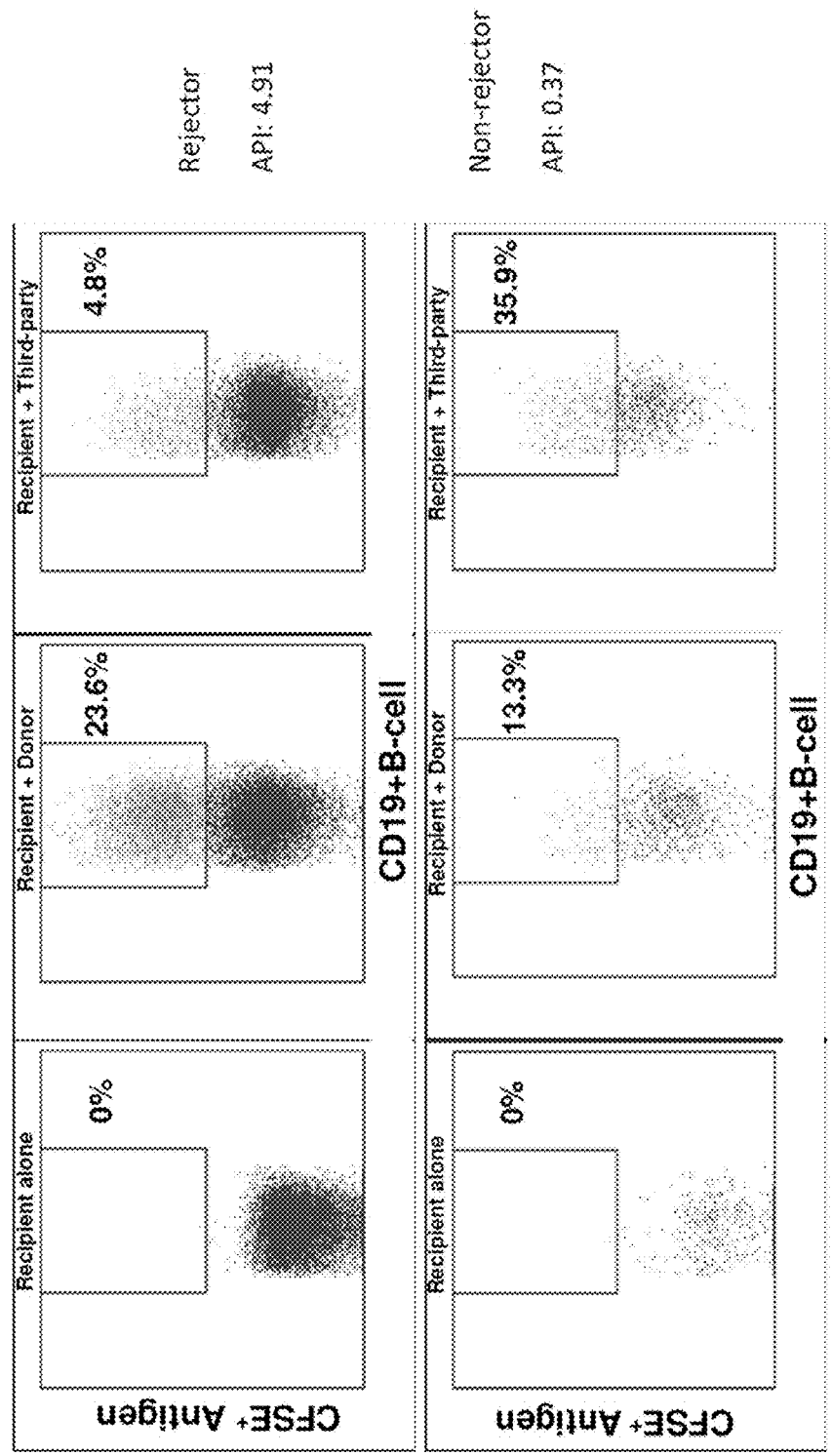
FIG. 1 is a series of scatterplots of flow cytometry data illustrating antigen uptake in rejectors versus non-rejectors. In the rejector (upper panels), 23.6% recipient B-cells present donor antigen (middle upper panel), compared with 4.8% recipient B-cells which present third-party antigen (right upper panel) for an API of 4.91. In the non-rejector (lower panels), 35.9% of recipient B-cells present third-party antigen (lower right panel), but only 13.3% present donor antigen (lower middle panel). The API is 0.37 in this non-rejector.

I. Abbreviations
　ACR: acute cellular rejection
　APC: antigen presenting cell
　API: antigen presenting index
　CD: cluster of differentiation
　HR: humoral rejection
　LTx: liver transplantation
　MLR: mixed lymphocyte response
　OVA: ovalbumin
　PBL: peripheral blood leukocytes
　SBTx: small bowel transplantation II. Terms The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Allograft: A transplant of an organ, tissue, bodily fluid or cell from one individual to a genetically nonidentical individual of the same species. As used herein, "allogeneic" encompasses a genetically different phenotype present in nonidentical individuals of the same species. Allogeneic examples include blood group phenotypes and immunoantigeneic allotypes. An "alloantigen" encompasses any antigen recognized by different individuals of the same species. Organisms, cells, tissues, organs, and the like from, or derived from, a single individual, or from a genetically identical individual are "autologous." "Transplant rejection" refers to a partial or complete immune response to a transplanted cell, tissue, organ, or the like on or in a recipient of the transplant due to an immune response to an allogeneic graft.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand that includes at least a light chain or heavy chain immunoglobulin variable region and specifically binds an epitope of an antigen. Antibodies can include monoclonal antibodies, polyclonal antibodies, or fragments of antibodies.

The term "specifically binds" refers to, with respect to an antigen, the preferential association of an antibody or other ligand, in whole or part, with a specific polypeptide. A specific binding agent binds substantially only to a defined target. It is recognized that a minor degree of non-specific interaction may occur between a molecule, such as a specific binding agent, and a non-target polypeptide. Nevertheless, specific binding can be distinguished as mediated through specific recognition of the antigen. Although selectively reactive antibodies bind antigen, they can do so with low affinity. Specific binding typically results in greater than 2-fold, such as greater than 5-fold, greater than 10-fold, or greater than 100-fold increase in amount of bound antibody or other ligand (per unit time) to a target polypeptide, such as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Antibodies can be composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

In some examples, antibodies are labeled, for example with a fluorescent marker that can aid in their detection.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term is used interchangeably with the term "immunogen." The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. T cells can respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as, 9, 10, 12 or 15 amino acids. The amino acids are in a unique spatial conformation. In one particular example, the antigen is an antigen obtained from a subject who is a donor, such as of an organ or of bone marrow, to another genetically different individual, such antigen is referred to as a donor antigen. In one example, the donor antigen includes antigens from lymphocytes, leukocytes, such as peripheral blood leukocytes or a combination thereof. In some examples, donor antigen includes lysed cell membranes from donor peripheral blood leukocytes, spleen cells, or bone marrow cells. In an example, donor antigen can be provided from a subject that had similar HLA-A, HLA-B, or HLA-DR loci profile as the donor. In other examples, the antigen is a third-party antigen (also referred to as a reference antigen). A third-party antigen is an antigen that was not obtained from the organ donor or organ recipient and has no similarity to the recipient or donor (as indicated by measuring HLA-A, HLA-B and HLA-DR loci). Exemplary third-party antigen samples include lymphocytes, leukocytes, such as peripheral blood leukocytes or a combination thereof. For example, third-party antigen samples include lysed cell membranes from donor peripheral blood leukocytes, spleen cells, or bone marrow cells. An autoantigen is an antigen that under normal conditions would not be a target of the immune system. However, the normal immunological tolerance for such an antigen is lost in a subject suffering from a specific autoimmune disease and stimulates the production of autoantibodies.

Antigen Presenting Cells (APCs): Highly specialized cells that can process antigens and display their peptide fragments on the cell surface together with molecules required for lymphocyte activation. For example, an APC is a cell that can present antigen bound to MHC class I or class II molecules to T cells. APCs include, but are not limited to, monocytes, macrophages, dendritic cells, B cells, T cells and Langerhans cells. A T cell that can present antigen to other T cells (including CD4+ and/or CD8+ T cells) is an antigen presenting T cell (T-APC).

Antigen Presenting Index (API): A measure of the uptake (either binding or internalization) of donor antigen in APCs of a subject, expressed as a ratio with the uptake of third-party antigen in APCs of the subject. An API>1 indicates an increased risk of rejection or the presence of rejection in the subject. An API<1 indicates a decreased risk of rejection or the absence of rejection in a subject. The API normalizes donor antigen uptake to the uptake of a reference (third-party) antigen for each person. The API is unique for each individual, but comparable between individuals.

B-cell: One of the two major types of lymphocytes. B-cells arise from bone marrow progenitor cells, which progress through multiple stages such as the pro-, pre- and transitional stages into the naive B-cell. The antigen receptor on B lymphocytes is a cell-surface immunoglobulin molecule. Upon activation by an antigen, B-cells differentiate into cells producing antibody of the same specificity as their initial receptor. B cells are also APCs.

An "immature B cell" is a cell that can develop into a mature B cell. Generally, pro-B cells (that express, for example, CD10) undergo immunoglobulin heavy chain rearrangement to become pro B pre B cells, and further undergo immunoglobulin light chain rearrangement to become an immature B cells. Immature B cells include T1 and T2 B cells. Thus, one example of an immature B cell is a T1 B that is an $AA41^{hi}CD23^{lo}$ cell. Another example of an immature B cell is a T2 B that is an $AA41^{hi}CD23^{hi}$ cell. Thus, immature B cells include B220 expressing cells wherein the light and the heavy chain immunoglobulin genes are rearranged, and that express AA41. Immature B cells can develop into mature B cells, which can produce immunoglobulins (e.g., IgA, IgG or IgM). Mature B cells express characteristic markers such as CD21 and CD23 ($CD23^{hi}CD21^{hi}$ cells), but do not express AA41. In some examples, a B cell is one that expresses $CD179^{hi}$, CD24, CD38 or a combination thereof. B cells can be activated by agents such as lippopolysaccharide (LPS) or IL-4 and antibodies to IgM.

B-cells have many functions. For example, a B-cell can serve as an APC (which activates T-cytotoxic cells toward effector function), activate naive or memory Th1 cells, or evolve into long-lived memory cell and transform into an antibody secreting plasma cell with T-cell help, and perpetuate antibody responses to autoantigens. Antigen is sensed by the B-cell via the B-cell receptor, or the immunoglobulin molecule.

CD5: A B-cell marker, also referred to as "cluster of differentiation 5." $CD5^+$ B-cells are a class of atypical, self-renewing B cells found mainly in the peritoneal and pleural cavities in adults and which have a far less diverse receptor repertoire than conventional B cells.

CD10: A B-cell marker. CD10 is primarily expressed on early B-cells and B-cell blasts, as well as T-cell precursors and bone marrow stromal cells. CD10 is an antigen that is a cell surface marker used in the diagnosis of human acute lymphocytic leukemia (ALL). CD10 is also known as membrane metallo-endopeptidase (MME) and CALLA.

CD27: A protein expressed on medullary thymocytes, T-cells, natural killer (NK) cells and some B-cells. CD27 is a member of the TNF-receptor superfamily. This receptor is involved in the generation and long-term maintenance of T cell immunity. It binds to ligand CD70, and plays a role in regulating B-cell activation and immunoglobulin synthesis. CD27 transduces signals that lead to the activation of NF-κB and MAPK8/JNK.

CD154: A protein expressed on T-cells. CD154 is also known as CD40 ligand. CD154 regulates B-cell function by engaging CD40 on the B-cell surface. A defect in this gene results in an inability to undergo immunoglobulin class switch and is associated with hyper-IgM syndrome.

Contacting: Placement in direct physical association; includes both in solid and liquid form.

Diagnosis: The process of identifying a disease by its signs, symptoms and results of various tests. The conclusion reached through that process is also called "a diagnosis." Forms of diagnostic testing commonly performed include blood tests, medical imaging, genetic analysis, molecular marker analysis, urinalysis, biopsy and histology. Diagnostic methods differ in their sensitivity and specificity. The "sensitivity" of a diagnostic assay is the percentage of diseased individuals (for example, individuals undergoing organ transplant rejection) who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it is effective if the method provides a positive indication that aids in diagnosis. "Prognostic" is the probability of development (or for example, the probability of severity) of a pathologic condition, such as organ rejection.

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser.

Examples of particular fluorophores that can be used in the disclosed methods are provided in U.S. Pat. No. 5,866,366 to Nazarenko et al. (which is hereby incorporated by reference in its entirety), such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56- carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Other suitable fluorophores include those known to those skilled in the art, for example those available from Molecular Probes (Eugene, Oreg.). In particular examples, a fluorophore is carbosyflouresciensuccinimyldiester.

Graft-Versus-Host Disease (GVHD): A common and serious complication of bone marrow or other tissue transplantation wherein there is a reaction of donated immunologically competent lymphocytes against a transplant recipient's own tissue. GVHD is a possible complication of any transplant that uses or contains stem cells from either a related or an unrelated donor.

There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines.

IgA: An antibody isotype that plays a critical role in mucosal immunity. More IgA is produced in mucosal linings than all other types of antibody combined. There are two subclasses of IgA (IgA1 and IgA2) and can exist in a dimeric form called secretory IgA (sIgA). In its secretory form, IgA is the main immunoglobulin found in mucous secretions, including tears, saliva, colostrum and secretions from the genito-urinary tract, gastrointestinal tract, prostate and respiratory epithelium. It is also found in small amounts in blood. The secretory component of sIgA protects the immunoglobulin from being degraded by proteolytic enzymes, thus sIgA can survive in the harsh gastrointestinal tract environment and provide protection against microbes that multiply in body secretions.

IgD: An antibody isotype that makes up about 1% of proteins in the plasma membranes of immature B-lymphocytes where it is usually coexpressed with another cell surface antibody called IgM. IgD is also produced in a secreted form that is found in very small amounts in blood serum. Secreted IgD is produced as a monomeric antibody with two heavy chains of the delta ($\delta$) class, and two immunoglobulin light chains.

IgM: An antibody isotype that is present on B cells. IgM is the largest type of antibody molecule in the human circulatory system. It is produced after an animal has been exposed to an antigen for an extended time or when an animal is exposed to an antigen for the second time.

Immune response: A response of a cell of the immune system, such as a B cell, or a T cell, to a stimulus. In one embodiment, the response is specific for a particular antigen (an "antigen-specific response").

A "parameter of an immune response" is any particular measurable aspect of an immune response, including, but not limited to, cytokine secretion (IL-6, IL-10, IFN-$\gamma$, etc), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. Similarly, an inhibition or decrease in a parameter of the immune response is a significant decrease in this parameter as compared to a control. Specific, non-limiting examples of a substantial decrease are at least about a 50% decrease, at least about a 75% decrease, at least about a 90% decrease, at least about a 100% decrease, at least about a 200% decrease, at least about a 300% decrease, and at least about a 500% decrease. A statistical test, such as a non-paramentric ANOVA, can be used to compare differences in the magnitude of the response induced by one agent as compared to the percent of samples that respond using a second agent. In some examples, $p<0.05$ is significant, and indicates a substantial increase or decrease in the parameter of the immune response. One of skill in the art can readily identify other statistical assays of use.

Immunocompromised subject: A subject who is incapable of developing or unlikely to develop a robust immune response, usually as a result of disease, malnutrition, or immunosuppressive therapy. An immunocompromised immune system is an immune system that is functioning below normal. Immunocompromised subjects are more susceptible to opportunistic infections, for example viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressives, and those who are receiving chemotherapy for cancer Immunocompromised individuals also includes subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also may be immunocompromised.

Infectious disease: Any disease caused by an infectious agent. Examples of infectious pathogens include, but are not limited to: viruses, bacteria, *mycoplasma* and fungi. In a particular example, it is a disease caused by at least one type of infectious pathogen. In another example, it is a disease caused by at least two different types of infectious pathogens. Infectious diseases can affect any body system, be acute (short-acting) or chronic/persistent (long-acting), occur with or without fever, strike any age group, and overlap each other. Infectious diseases can be opportunistic infections, in that they occur more frequently in immuno-compromised subjects Viral diseases commonly occur after immunosuppression due to re-activation of viruses already present in the recipient. Particular examples of viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C. Opportunistic infections occur in a subject with a compromised immune system, such as a subject who has been immuno-depleted and recently received a bone marrow transplant or a hematopoietic stem cell transplant. These infections include, but are not limited to cytomegalovirus, *Candida albicans*, human immunodeficiency virus, *Staphylococcus aureus*, *Steptococcus pyogenes*, *Pseudomas aeruginosa*, *Acinteobacter baumanni*, *Toxoplasma gondii*, *Pneumocystitis carinii*, or *Aspergillus* infections.

Additional examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans*, *Histoplasma capsulatum*, *Coccidioides immitis*, *Blastomyces dermatitidis*, *Chlamydia trachomatis*, *Candida albicans*.

Examples of infectious bacteria include: *Helicobacter pyloris*, *Borelia burgdorferi*, *Legionella pneumophilia*, *Mycobacteria* sps (such as. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus influenzae*, *Bacillus anthracia*, *corynebacterium diphtherias*, *corynebacterium* sp., *Erysipelothrix rhusiopathiae*, *Clostridium perfringens*, *Clostridium tetani*, *Enterobacter aerogenes*, *Klebsiella pneumoniae*, *Pasteurella multocida*, *Bacteroides* sp., *Fusobacterium nucleatum*, *Streptobacillus moniliformis*, *Treponema pallidum*, *Treponema pertenue*, *Leptospira*, and *Actinomyces israelii*. Other infectious organisms (such as protists) include: *Plasmodium falciparum* and *Toxoplasma gondii*.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. Similarly, an "isolated" cell has been substantially separated, produced apart from, or puified away from other cells of the organism in which the cell naturally occurs. Isolated cells can be, for example, at least 99%, at leat 98%, at least 95%, at least 90%, at least 85%, or at least 80% pure.

Label: An agent capable of detection, for example by ELISA, spectrophotometry, mass spectrometry, flow cytometry, or microscopy. For example, a label can be attached to a molecule, thereby permitting detection of the molecule. In one particular example, a label is attached to an antibody. Examples of labels include, but are not limited to, radioactive isotopes, enzyme substrates, co-factors, ligands, chemiluminescent agents, fluorophores, haptens, enzymes, metals, metal isotopes and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In a particular example, donor and third-party antigens are labeled with a fluorophore, such as carboxyflouresciensuccinimyldiester to allow antigen detection by flow cytometry.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes).

Lymphocytes: A type of white blood cell that is involved in the immune defenses of the body. The main types of lymphocytes are: B cells, T cells and natural killer cells (NK cells). "T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8

T cell is a cytotoxic T lymphocyte. In another embodiment, a CD8 cell is a suppressor T cell.

Major Histocompatability Complex (MHC): A generic designation meant to encompass the histocompatability antigen systems described in different species, including the human leukocyte antigens ("HLA").

Organ rejection or transplant rejection: Functional and structural deterioration of an organ due to an active immune response expressed by the recipient, and independent of non-immunologic causes of organ dysfunction.

Sample (or biological sample): A biological specimen containing genomic DNA, RNA (including mRNA and microRNA), protein, cells, tissues or combinations thereof, obtained from a subject. Examples include, but are not limited to, peripheral blood, urine, saliva, tissue biopsy, fine needle aspiration samples, surgical specimen, and autopsy material. In one example, a sample is blood sample which includes lymphocytes, leukocytes, such as peripheral blood leukocytes, or a combination thereof with or without red blood cells.

Subject: Living multi-cellular vertebrate organisms, a category that includes human and non-human mammals. In one particular example, the subject is a child. As used herein, a "child" refers to a person under the age of 18.

T-Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutic agent: A chemical compound, small molecule, or other composition, such as an antisense compound, antibody, protease inhibitor, hormone, chemokine, cytokine, radioactive agent, or anti-inflammatory agent, capable of inducing a desired therapeutic or prophylactic effect when properly administered to a subject.

Therapeutically effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

Under conditions sufficient to: A phrase that is used to describe any environment that permits the desired activity. In one example, includes conditions sufficient to induce uptake of a molecule, such as the binding or internalization of an antigen by a cell (e.g., the binding and/or internalization of donor antigen by an APC.

III. Methods for Diagnosing or Predicting Organ Transplant Rejection or GVHD

Disclosed herein is an assay for diagnosis and prediction of B-cell rejection, such as transplant rejection or in GVHD. This assay exploits the fact that a B-cell is a potent APC. Monitoring antigen uptake and presentation by the APCs serves as an early warning for whether the effector response favors ACR, or HR, or a rejection-free state. The disclosed B-cell antigen presenting test has several uses in transplantation. In some examples, the assay is used to measure the risk of rejection to manage anti-rejection drug therapy. In some examples, the assay is used to calculate the time to reduction of rejection-risk or API<1 when estimating time to reduction of immunosuppressive drugs including but not limited to steroids, tacrolimus, etc. or comparing two different anti-rejection drug regimens, or two different types of transplant recipients. In some examples, the assay is used to estimate the severity of rejection. For example, the API is higher with rejection of higher severity which requires more intensive anti-rejection drug therapy. In some examples, the disclosed assay is used to estimating the likelihood of graft loss. In some examples, the disclosed assay is used to establish a personalized rejection risk estimate at any given time from an individual recipient in which the same donor or surrogate donor stimulator is used, and the same third-party antigen is used as a reference for donor antigen presentation for the same transplant recipient. In some examples, the disclosed assay is used in combination a variety of markers, which are unique to the different developmental stages of the B-cell, B-cell antigen presentation can be used to determine when naïve B-cells have transitioned into memory IgG+B-cell. This transition from naïve to memory IgG+B-cells is characterized by the decrease or loss of antigen presenting function. For this utility, several B-cell lineage-specific markers can be used.

In some embodiments, the subject is a human. In particular examples, the subject is a human child, such as a child of zero to five years of age, less 10 years of age, less than 13 years of age, or less than 18 years of age. In other embodiments, the subject is an adult subject, such as a subject greater than 18 years of age, greater than 20 years of age or greater than 25 years of age. In other embodiments, the subject is a non-human animal, such as a veterinary subject (for example, a small or large domestic animal).

The presently disclosed assay has significantly higher sensitivity and specificity than previously disclosed assays. For example, previous studies have evaluated B-cell and other APC functions by incubating APCs with a non-specific antigen, ovalbumin (OVA) in which OVA uptake was used as a measure of antigen presentation. The sensitivity and specificity of B-cell OVA uptake was 70-75% for association with rejection-prone (Rejector) status. However, for clinical implementation, a more sensitive and specific test is needed.

In some examples, a method of assessing organ rejection is disclosed. It is contemplated that the transplant can be any organ, including solid organs. In some examples, the subject has received the transplant. In some examples, the subject is a candidate to receive the transplant. Examples of solid organs include, but are not limited to, liver, intestine, kidney, heart, lung, pancreas and skin. In the context of the present disclosure, a transplanted organ need not be the entire organ, but can be a portion or section of the organ. In particular examples, the subject has received, or is in need or receiving, multiple organs, or portions of multiple organs. In some cases, the subject is a transplant recipient or candidate for a transplant of a combination of two or more of a solid organ, bone marrow and stem cells. In some cases, the subject is undergoing treatment, including immunosuppressive therapy.

In some examples, the method includes contacting a first sample comprising APCs obtained from a subject in need of or having received an organ transplant from a donor, with a donor antigen from the donor, under conditions sufficient to induce uptake of the donor antigen; contacting a second sample comprising APCs obtained from the subject in need of or having received an organ transplant, with a third-party antigen, under conditions sufficient to induce uptake of the third-party antigen; and determining the ratio of uptake of the donor antigen in the first sample to uptake of the third-party antigen in the second sample. A ratio of greater than one indicates organ rejection in the subject or a predisposition for organ rejection. In some embodiments, the APCs are B cells.

In some embodiments, methods are for assessing rejection of a solid organ transplant. These assays measure the uptake of donor antigen and express it as a ratio with uptake of third-party antigen in APCs, such as B cells. This ratio is the API. An API>1 indicates increased risk of rejection or the presence of rejection. For example, and API of greater than 1.2, greater than 1.5, greater than 1.75, greater than 2, greater than 3, greater than 4, greater than 5, greater than 6, greater than 7, greater than 8, greater than 9, or greater than 10, such as between 1.2-10, 5-10, 1.2-3, 1.5-2.5, including 1.25, 1.3, 1.4, 1.5, 1.6, 1.7, 1.8, 1.9, 2, 2.5, 3, 3.5, 4. 4.5, 5, 5.5, 6, 6.5, 7, 7.5, 8, 8.5, 9, 9.5, 10 or more can indicate increased risk of rejection. An API<1 indicates decreased risk of rejection or rejection. For example, and API of less than 0.9, less than 0.8, less than 0.75, less than 0.6, less than 0.5, less than 0.1 or less than 0.01, such as between 0.2 and 0.9, 0.3 and 0.8, 0.4 and 0.7, 0.5 and 0.6, including 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.60, 0.65, 0.7, 0.75, 0.8, 0.85, 0.9, 0.95 can indicate a decreased risk of rejection. The API is unique in that it "normalizes" donor antigen uptake to the uptake of a reference (third-party) antigen for each person. In this way, the API is unique for each individual, and yet comparable between individuals, on the basis of this normalized scale.

Also provided herein is a method of assessing GVHD. In some examples, the method includes contacting a first sample comprising APCs obtained from a sample of donor bone marrow or stem cells before transplantation, or from the recipient who has received donor bone marrow or stem cells. The method includes contacting APCs from the subject following transplantation, with a recipient antigen from the recipient, under conditions sufficient to induce uptake of the recipient antigen; contacting a second sample comprising APCs obtained from a sample of donor bone marrow or stem cells before transplantation, or from the recipient who has received donor bone marrow or stem cells,—with a third-party antigen, under conditions sufficient to induce uptake of the third-party antigen; and determining the ratio of uptake of the recipient antigen in the first sample to uptake of the third-party antigen in the second sample. A ratio of greater than one indicates GVHD in the subject or a predisposition for GVHD. In some embodiments, the APCs are B cells.

In some embodiments, the methods for assessing GVHD include measuring the uptake of recipient antigen and expressing it as a ratio with uptake of third-party antigen in APCs, such as B cells, to determine the API. An API>1 indicates increased risk of GVHD or the presence of GVHD. For example, and API of greater than 1.2, greater than 1.5, greater than 1.75, greater than 2, greater than 3, greater than 4, greater than 5, greater than 6, greater than 7, greater than 8, greater than 9, or greater than 10, such as between 1.2-10, 5-10, 1.2-3, 1.5-2.5, including 1.25, 1.3, 1.4, 1.5, 1.6, 1.7, 1.8, 1.9, 2, 2.5, 3, 3.5, 4. 4.5, 5, 5.5, 6, 6.5, 7, 7.5, 8, 8.5, 9, 9.5, 10 or more can indicate increased risk of GVHD. An API<1 indicates decreased risk of GVHD or GVHD. For example, an API of less than 0.9, less than 0.75, less than 0.5, less than 0.1 or less than 0.01, such as between 0.2 and 0.9, 0.3 and 0.8, 0.4 and 0.7, 0.5 and 0.6, including 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.60, 0.65, 0.7, 0.75, 0.8, 0.85, 0.9, 0.95 can In some examples, the disclosed assays predict B-cell rejection with a sensitivity of at least 90% and a specificity of at least 90% for an increased risk of B-cell rejection or the presence of B-cell rejection. In some examples, the methods disclosed herein have a sensitivity of at least 90%, at least 91%, at least 92%, at least 93%, at least 94%, at least 95%, at least 96%, at least 97%, at least 98% or at least 99%, including between 90% to 98%, between 92% to 96%, between 92% to 95%, between 93% and 95%, between 94% and 96%, including 90%, 91%, 92,%, 93%, 94%, 95%, 96%, 97%, 98%, or 99% sensitivity. In some examples, the methods disclosed herein have a specificity of at least 90%, at least 91%, at least 92%, at least 93%, at least 94%, at least 95%, at least 96%, at least 97%, at least 98% or at least 99%, including between 90% to 98%, between 92% to 96%, between 92% to 95%, between 93% and 95%, between 94% and 96%, including 90%, 91%, 92,%, 93%, 94%, 95%, 96%, 97%, 98%, or 99% specificity.

In some embodiments of the method, an API of greater than one predicts rejection with a sensitivity of approximately 94%, 95%, 96%, 97%, 98% or 99% and/or a specificity of approximately 94%, 95%, 96%, 97%, 98% or 99%.

In some embodiments, comparing uptake of the donor (or recipient antigen) to uptake of the third party antigen further includes labeling a biological sample comprising donor (or recipient) antigen and a biological sample comprising third party antigen with a detectable label. Any type of detectable label can be used to facilitate detection. Specific, non-limiting examples of labels include fluorescent tags, enzymes, and radioactive isotopes. Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser.

Examples of particular fluorophores that can be used in the methods disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate;

Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Other suitable fluorophores include those known to those skilled in the art, for example those available from Molecular Probes (Eugene, Oreg.). In some examples, the fluorescent molecule is carboxyfluoresceinsuccinimidyl ester or other like compounds.

The method includes determining the ratio of uptake of the donor (or recipient) antigen in the first sample to uptake of the third-party antigen in the second sample by measuring the fluorescence of the two samples.

In one embodiment, uptake can be measured by fluorescent activated cell sorting (FACS). FACS employs a plurality of color channels, low angle and obtuse light-scattering detection channels, and impedance channels, among other more sophisticated levels of detection, to separate or sort cells. Any FACS technique may be employed as long as it is not detrimental to the viability of the desired cells (for exemplary methods of FACS see U.S. Pat. No. 5,061,620, herein incorporated by reference).

For example, the sample including APCs is obtained from blood, spleen or bone marrow. In some embodiments, the first sample and/or the second sample that contain APCs are peripheral blood lymphocytes or peripheral blood leukocytes.

The antigen can be a purified or isolated antigen. Thus, the antigen can be synthesized or produced by molecular biology techniques. The donor antigen can be any antigen of interest from the donor. One isolated antigen, or more than one isolated antigen, such as at least two, at least three, at least four, at least 5, at least 10 or more isolated antigens can be utilized.

In some examples, the antigen is included in a complex biological sample, such as a cell lysate or fraction. In some examples, the antigen is a cell lysate of lymphocytes and/or leukocytes. In some embodiments, the donor antigen or the third-party antigen include donor cells, an antigenic peptide, an antigenic peptide labeled with a fluorochrome, or any combination thereof.

In some embodiments, for assessing transplant rejection, one antigen at the HLA-A, HLA-B or HLA-DR loci from the donor is utilized in the method. In some embodiments, more than one antigen at the HLA-A, HLA-B or HLA-DR loci from the donor is utilized in the method. In further embodiments, a combination of antigens from the HLA-A, HLA-B and HLA-DR loci are utilized in the methods. In one example, the donor antigen includes antigens from lymphocytes, leukocytes, such as peripheral blood leukocytes or a combination thereof. In some examples, donor antigen includes lysed cell membranes from donor peripheral blood leukocytes, spleen cells, or bone marrow cells. In an example, donor antigen is provided from a subject that has the same or very similar HLA-A, HLA-B, or HLA-DR loci profile as the donor, but is not the donor.

In other embodiments, for assessing GVHD, one antigen at the HLA-A, HLA-B or HLA-DR and other HLA loci from the recipient is utilized in the method. In other embodiments, more than one antigen at the HLA-A, HLA-B or HLA-DR loci from the recipient is utilized in the method to detect GVHD. In further embodiments, a combination of antigens from the HLA-A, HLA-B and HLA-DR and other HLA loci are utilized in this method. In one example, the recipient antigen includes antigens from lymphocytes, leukocytes, such as peripheral blood leukocytes or a combination thereof. In some examples, recipient antigen includes lysed cell membranes from recipient peripheral blood leukocytes, spleen cells, or bone marrow cells. In an example, recipient antigen is provided from a subject that had the same of very similar HLA-A, HLA-B, or HLA-DR and other HLA loci profile as the recipient, but is not the recipient. In one example, minor HLA antigens other than or in addition to HLA-A, -B and -DR are utilized.

The third party antigen can be from any subject who is allogeneic to both the donor and the recipient. One antigen or more than one antigen can be utilized. In some embodiments, one antigen at the HLA-A, HLA-B or HLA-DR and other HLA loci from a third party is utilized in the method. In other embodiments, more than one antigen at the HLA-A, HLA-B or HLA-DR and other HLA loci from the third party is utilized in the method. In further embodiments, a combination of antigens from the HLA-A, HLA-B and HLA-DR and other HLA loci are utilized in the methods. Exemplary third-party antigen samples also include lymphocytes, leukocytes, such as peripheral blood leukocytes or a combination thereof. For example, third-party antigen samples include lysed cell membranes from third party peripheral blood leukocytes, spleen cells, or bone marrow cells.

In some embodiments, the method is used to titrate the dose of an immunosuppressive agent provided to the subject or evidence the effectiveness of an immunosuppressive regimen for the treatment of transplant rejection. For example, a subject is given a first treatment with an immunosuppressive regimen. A first sample including APCs, such as B cells is obtained from a subject having received an organ transplant from a donor is contacted with a donor antigen from the donor, under conditions sufficient to induce uptake of the donor antigen. A second sample including APCs, such as B cells, obtained from the subject is contacted with a third-party antigen, under conditions sufficient to induce uptake of the third-party antigen. The ratio of uptake of the donor antigen in the first sample to uptake of the third-party antigen in the second sample is determined A ratio of greater than one indicates organ rejection in the subject and indicates that immunosuppression should be increased, or that a different immunsuppressive regimen should be used. A ratio of less than one indicates the absence of organ rejection in the subject and indicates that immunosuppression can be maintained or decreased, or indicates that the immunsuppressive regimen is appropriate for the subject. The methods can be repeated, so that the subject is monitored regularly. For example, the method can be repeated daily, bi-weekly, weekly, bi-monthly, or monthly. The immunosuppressive agent can include, but is not limited to, a steriod, cyclosporine A, anti-CD3, anti-CD25 (such as daclizumbab), cytokines, rapamycin, or any other immunosuppressive agent of interest including but not limited to tacrolimus, bortezimib, alemtuzumab, anti-human thymocyte globulin, anti-lymphocyte globulin, mycophenolate mofetil, etc.

In some embodiments, the method is used to assess the degree of organ rejection. For example, a higher API is associated with more severe rejection than with mild rejection. To illustrate further, a higher API is associated with steroid-resistant than with steroid-sensitive rejection.

In some embodiments, the method is used to titrate the dose of an immunosuppressive agent provided to the subject or evidence the effectiveness of an immunosuppressive regimen for treatment of GVHD. For example, a subject is given a first treatment with an immunosuppressive regimen. A first sample comprising APCs, such as B cells is obtained from a subject having received an organ transplant from a donor is contacted with a recipient antigen from the recipient, under conditions sufficient to induce uptake of the recipient antigen. A second sample comprising APCs, such as B cells, obtained from the subject is contacted with a third-party antigen, under conditions sufficient to induce uptake of the third-party antigen. The ratio of uptake of the recipient antigen in the first sample to uptake of the third-party antigen in the second sample is determined A ratio of greater than one indicates GVHD in the subject and indicates that immunosuppression should be increased, or that a different immunsuppressive regimen should be used. A ratio of less than one indicates the absence of GVHD in the subject and indicates that immunosuppression can be maintained or decreased, or indicates that the immunsuppressive regimen is appropriate for the subject. API numbers <0.9, or <0.1 indicate decreased risk, while API>1.2 or >2 or >3 would indicate increased risk of GVHD. The methods can be repeated, so that the subject is monitored regularly. For example, the method can be repeated daily, bi-weekly, weekly, bi-monthly, or monthly. The immunosuppressive agent can include, but is not limited to, a steriod, cyclosporine A, anti-CD4, anti-CD25 (such as daclizumbab), cytokines, rapamycin, or any other immunosuppressive agent of interest including but not limited to tacrolimus, bortezimib, alemtuzumab, anti-human thymocyte globulin, anti-lymphocyte globulin, mycophenolate mofetil, etc.

In some embodiments of the method, for detecting transplant rejection, determining the ratio of uptake of the donor antigen in the first sample to uptake of the third-party antigen in the second sample includes detecting a plurality of biomarkers following treatment with the donor antigen with the first sample comprising antigen presenting cells and the third-party antigen with the second sample comprising antigen presenting cells, and comparing the expression of the plurality of biomarkers following treatment with donor antigen to the expression of the biomarkers following treatment with the third-party antigen to determine the API. For example, markers categorize a B-cell as memory or naive or as plasma cell precursors, based on whether they express CD27, IgA, IgM, IgG, IgD, CD25, CD5, CD10, CD154, CD138, CD19, CD38, CD24, CTLA4, etc. In other embodiments, for detecting GVHD, determining the ratio of uptake of the recipient antigen in the first sample to uptake of the third-party antigen in the second sample includes detecting a plurality of biomarkers on the antigen presenting cells following treatment with the recipient antigen with the first sample comprising antigen presenting cells and the third-party antigen with the second sample comprising antigen presenting cells, and comparing the expression of the plurality of biomarkers following treatment with recipient antigen to the expression of the biomarkers following treatment with the third-party antigen to determine the antigen presenting index.

In some examples, the plurality of biomarkers includes at least one of CD27, IgM, IgA, IgD, CD5, CD10, such as one, two, three, four, five or all six markers. In other examples, additional biomarkers such memory cell markers, plasma cell markers, B-cell activation markers, leukocyte/lymphocyte markers, cell viability markers, and other markers known to those of skill in the art to be useful in monitoring organ transplant rejection. In some examples, additional markers included IgG (memory cell marker), CD19, CD38 (plasma cell marker), CD138 (plasma cell activation markers), CD154 (B-cell activation marker), CTLA4 (negative B-cell co-stimulator marker), CD45 (pan-leukocyte/lymphocyte marker) or any combination thereof. Thus, the method can also include measuring B and T cells, such as memory T cells that express CTLA4 or CD154 and/or CD154+CD19+B cells.

In one embodiment, the method includes assessing the API and the number of inflammatory donor-specific B cells, which express CD154. In other example, the method includes assessing the API and the number of CTLA4+ T-cytotoxic memory T cells. In a further example, the method includes measuring the API and the number of CD154+CD19+B cells. In one example, API is positively correlated with inflammatory donor specific B cells, which express CD154 and CD19. As such, an API greater than one indicates increased CD154+ and CD19 cells in the recipient sample. In another example, API is negatively correlated with anti-inflammatory donor specific T cytotoxic memory cells expressing CTLA4. In this example, an API greater than one indicates fewer CTLA4 T cells in the donor sample. In a further example, API is negatively correlated with anti-inflammatory donor specific B cells expressing the marker CTLA4 in which an API index greater than one indicates fewer CTLA4 B cells in the donor sample. The method can include measuring one or more of these cell types.

In some examples, the plurality of biomarkers includes at least CD27, IgM, IgA, IgD, IgG, CD5 and CD10. It is contemplated that additional biomarkers can also be detected, such as early B-cell lineage markers, CD24, and CD179b, additional memory cell markers (e.g., IgG), CD19, CD38 (plasma cell marker), and CD138 (plasma cell activation markers), CD154 (B-cell activation marker), CTLA4 (negative B-cell co-stimulator marker), CD45 (pan-leukocyte/lymphocyte marker), CD25, CD3, 7-AAD, CD69, CD71, CD86 IFN gamma, IL-2, TNF alpha, CD45RA, CCR7 and CD54. Thus, in some embodiments, the method includes measuring the number of B cells that express one or more of CD27, IgM, IgA, IgG, IgD, CD5 and CD10. In other embodiments, the method includes measuring the number of memory B cells, plasma cells, or activated B cells. In some examples, IgD+B-cells are considered to be naive B-cells. In other examples, a CD27+ or an IgG+B-cell is considered to be a memory B-cell. In some examples, additional biomarkers include one or more B-cell markers disclosed in Linas et al. (*Immunology Letters* 134: 113-121, 2011) which is hereby incorporated by reference in its entirety.

In some embodiments, expression levels of the plurality of biomarkers are measured using FACS. Any FACS technique (including variants based on principles of flow cytometry e.g., mass spectrometric visualization of cellular markers with metallic ligands) or any other cellular imaging may be employed as long as it is not detrimental to the viability of the desired cells (for exemplary methods of FACS see U.S. Pat. No. 5,061,620, herein incorporated by reference).

However, other techniques of differing efficacy may be employed to isolate and enumerate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required. Separation procedures may include magnetic separation, using antibody-coated paramagnetic beads, affinity chromatography, cytotoxic agents, either joined to a monoclonal antibody or used in conjunction with complement, and "panning", which utilizes a monoclonal antibody attached to a solid matrix, or another convenient technique. Antibodies attached to paramagnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (such as an antigen that binds one or more of the monoclonal antibodies disclosed herein) to bind to the solid-phase linked antibodies. The bound cells are then separated from the solid phase by any appropriate method, depending mainly upon the nature of the solid phase and the antibody employed.

In one example, the presence and quantity of the various biological markers are measured by labeling the cells with marker specific colored dyes which are able to be detected and differentiated by a flow cytometer. Dyes known to those of ordinary skill in the art, such as carboxy fluorescein diacetate succimidyl ester (CFSE, Molecular Probes, Eugen, Oreg.), EMA (cell viability dye), 7-AAD (cell viability dye) and Quantum dots, such as having emission spectra between 545 nm and 800 nm (Quantum Dot Corp. Hayward, Calif.), can be used to detect the desired markers.

While any suitable equipment and methodology for measuring the multiple parameters can be employed, in one example a flow cytometer is used. Flow cytometers capable of detecting and differentiating at least 4 (and more preferably at least 7) differently colored markers are employed. In some examples, a flow cytometer capable of detecting and differentiating at least 10, such as at least 15, at least 20, or at least 30 different colored markers is employed. In some examples, a flow cytometer capable of measuring and comparing in at least 25 or more multiple parameters, such as in excess of 50 multiple parameters or even over 100 multiple parameters is utilized. These flow cytometric capabilities exist in novel mass spectrometry platforms which detect metal dye labels. Methods of using a flow cytometric machine are known to hose of skill in the art.

IV. Additional Methods

The disclosed methods can also be used to determine the B-cell response to other antigens, including antigens from allergens, infectious pathogens, tumors or associated with autoimmune diseases/disorders. Infectious pathogens include bacteria, fungi, protists, prions and/or viruses. These additional uses can be either alone or in addition to diagnosing or predicting organ transplant rejection.

In some embodiments, the method is used to detect reactivity to an antigen from a pathogen. For example, the method includes determining an API by comparing uptake of an antigen from a first pathogen to uptake of an antigen from a second (reference) pathogen by APCs from a subject of interest. An API>1 indicates increased likelihood of infection with the first pathogen and a decreased likelihood of infection with the second pathogen. For example, and API of greater than 1.2, greater than 1.5, greater than 1.75, greater than 2, greater than 3, greater than 4, greater than 5, greater than 6, greater than 7, greater than 8, greater than 9, or greater than 10 can indicate increased likelihood of infection with the first pathogen. An API<1, such as between 0.1 to 0.95 or 0.3 to 0.85, indicates a decreased likelihood of infection with the first pathogen, and an increased likelihood of infection with the second pathogen. For example, and API of less than 0.9, less than 0.75, less than 0.5, less than 0.1 or less than 0.1 can indicate a increased likelihood of an infection with the second pathogen, and a decreased likelihood of infection with the second pathogen.

In some embodiments of the method, determining the antigen presenting index comprises contacting a first portion of the biological sample comprising APCs obtained from a subject at risk of acquiring or known to have a particular disease or condition, such as a viral, fungal or bacterial infection, with a first antigen from a first viral, fungal, or bacterial pathogen, under conditions sufficient to induce uptake of the antigen; contacting a second portion of the biological sample comprising APCs obtained from the subject at risk of acquiring or known to have a particular disease or condition, with a second reference or a non-pathogenic antigen from different pathogen, under conditions sufficient to induce uptake of the second antigen; and determining the ratio of uptake of the first antigen in the first portion of the biological sample to uptake of the second antigen in the second portion of the biological sample. An increase in uptake of the first antigen as compared to the uptake of the second (reference) antigen indicates that the subject has an infection with the first pathogen. An increase in the uptake of the second antigen as compared to the uptake of the first antigen indicates that the subject has an infection with the second pathogen. Another way in which the uptake of a pathogenic antigen can indicate disease severity is if it exceeds a threshold established in patients with varying disease severity.

An API of greater than one indicates the presence of a particular condition, such as an infection with the first pathogen, with a sensitivity of at least 90% and indicates the presence of infection with specificity of at least 90% for the risk of infection or acquiring the disease or presence of infection or disease. In some examples, the methods disclosed herein have a sensitivity of at least 90%, at least 91%, at least 92%, at least 93%, at least 94%, at least 95%, at least 96%, at least 97%, at least 98% or at least 99%. In some examples, the methods disclosed herein have a specificity of at least 90%, at least 91%, at least 92%, at least 93%, at least 94%, at least 95%, at least 96%, at least 97%, at least 98% or at least 99%.

Similarly, an API of greater than one indicates the presence of a particular condition, such as an infection with the first pathogen, with a sensitivity of at least 90% and a indicates the presence of infection with specificity of at least 90% for the risk of infection or acquiring the disease or presence of infection or disease. In some examples, the methods disclosed herein have a sensitivity of at least 90%, at least 91%, at least 92%, at least 93%, at least 94%, at least 95%, at least 96%, at least 97%, at least 98% or at least 99%.

In some examples, the methods disclosed herein have a specificity of at least 90%, at least 91%, at least 92%, at least 93%, at least 94%, at least 95%, at least 96%, at least 97%, at least 98% or at least 99%.

The first and second pathogen of interest can be any allergen, bacteria, fungus or virus including those described herein.

i. Viral Pathogens

Specific examples of viral pathogens include without limitation any one or more of (or any combination of) Arenaviruses (such as Guanarito virus, Lassa virus, Junin virus, Machupo virus and Sabia), Ariteriviruses, Roniviruses, Astroviruses, Bunyaviruses (such as Crimean-Congo hemorrhagic fever virus and Hantavirus), Barnaviruses, Birnaviruses, Bornaviruses (such as Borna disease virus), Bromoviruses, Caliciviruses, Chrysoviruses, Coronaviruses (such as Coronavirus and SARS), Cystoviruses, Closteroviruses, Comoviruses, Dicistroviruses, Flaviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and OC43), human enteroviruses (such as human enterovirus A-D), human erythrovirus V9, human foamy viruses, human herpesviruses (such as human herpesvirus 1 (herpes simplex virus type 1), human herpesvirus 2 (herpes simplex virus type 2), human herpesvirus 3 (Varicella zoster virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpesvirus 8 type M, human herpesvirus 8 type P and Human Cyotmegalovirus), human immunodeficiency viruses (HIV) (such as HIV 1 and HIV 2), human metapneumoviruses, human papillomaviruses, human parainfluenza viruses (such as human parainfluenza virus 1-3), human parechoviruses, human parvoviruses (such as human parvovirus 4 and human parvovirus B19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picornaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, and Noroviruses among others.

Viral antigens may be from a Hepatitis C virus (HCV). HCV antigens may be selected from one or more of E1, E2, E1/E2, NS345 polyprotein, NS 345-core polyprotein, core, and/or peptides from the nonstructural regions (Houghton et al. (1991) *Hepatology* 14:381-388, which is incorporated by reference).

Viral antigens may be derived from a Human Herpes virus, such as Herpes Simplex Virus (HSV), Varicella-zoster virus (VZV), Epstein-Barr virus (EBV), or Cytomegalovirus (CMV). Human Herpes virus antigens may be selected from immediate early proteins, early proteins, and late proteins. HSV antigens may be derived from HSV-I or HSV-2 strains. HSV antigens may be selected from glycoproteins gB, gC, gD and gH, or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins. Exemplary herpes antigens include (GENBANK™ Accession No. in parentheses) those derived from human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), and human herpesvirus 8 type P (NC_009333).

Human Papilloma virus (HPV) antigens are known in the art and can be found for example in International Patent Publication No. WO96/19496, (incorporated by reference in its entirety) which discloses variants of HPV E6 and E7 proteins, particularly fusion proteins of E6/E7 with a deletion in both the E6 and E7 proteins. HPV L1 based antigens are disclosed in international Patent publication Nos. WO94/00152, WO94/20137, WO93/02184 and WO94/05792, all of which are incorporated by reference. Such an antigen can include the L1 antigen as a monomer, a capsomer or a virus like particle. Such particles may additionally comprise L2 proteins. Other HPV antigens are the early proteins, such as E7 or fusion proteins such as L2-E7. Exemplary HPV antigens include (GENBANK™ Accession No. in parentheses) those derived from human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-cand90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), and human papillomavirus type 96 (NC_005134).

Viral antigens may be derived from a Retrovirus, such as an Oncovirus, a Lentivirus or a Spumavirus. Oncovirus antigens may be derived from HTLV-I, HTLV-2 or HTLV-5. Lentivirus antigens may be derived from HIV-I or HIV-2. Retrovirus antigens may be selected from gag, pol, env, tax, tat, rex, rev, nef, vif, vpu, and vpr. Antigens for HIV are known in the art, for example HIV antigens may be selected from gag (p24gag and p55gag), env (gp160 and gp41), pol, tat, nef, rev vpu, miniproteins, (p55 gag and gp140v). HIV antigens may be derived from one or more of the following strains: HIVmb, HIV; HIVLAV, HIVLAI, HIVM N, HIV-1 CM235, HIV-1 US4. Examples of HIV antigens can be found in International Patent Publication Nos. WO09/089568, WO09/080719, WO08/099284, and WO00/15255, and U.S. Pat. Nos. 7,531,181 and 6,225,443, all of which are incorporated by reference. Exemplary HIV antigens include those derived from human immunodeficiency virus 1 (NC_001802), human immunodeficiency virus 2 (NC_001722).

ii. Allergens

Exemplary allergens (which are nonparasitic antigens capable of stimulating a type-I hypersensitivity reaction) include those derived from plants, such as trees, for example *Betula verrucosa* allergens Bet v 1, Bet v 2, and Bet v 4; *Juniperous oxycedrus* allergen Jun o 2; *Castanea sativa* allergen Cas s 2; and *Hevea brasiliensis* allergens Hev b 1, Hev b 3, Hev b 8, Hev b 9, Hev b 10 and Hev b 11; grasses, such as *Phleum pretense* allergens Phl p 1, Phl p 2, Phl p 4, Phl p 5a, Phl p 5, Phl p 6, Phl p 7, Phl p 11, and Phl p 12; weeds, such as *Parietaria judaica* allergen Par j 2.01011; and *Artemisia vulgaris* allergens Art v 1 and Art v 3; Mites, such as *Dermatophagoides pteronyssinus* allergens Der p 1, Der p 2, Der p 5, Der p 7, Der p 8, and Der p 10; *Tyrophagu putrescentiae* allergen Tyr p 2; *Lepidoglyphus destructor* allergens Lep d 2.01 and Lep d 13; and *Euroglyphus maynei* allergen Eur m 2.0101; animals, such as cats, for example *Felis domesticus* allergen Fel d 1; *Penaeus aztecus* allergen Pen a 1; *Cyprinus carpo* allergen Cyp c 1; and albumin from cat, dog, cattle, mouse, rat, pig, sheep, chicken, rabbit, hamster, horse, pigeon, and guinea pig; Fungi, such as *Penicillium citrinum* allergens Pen c 3 and Pen c 19; *Penicillium notatum* allergen Pen n 13; *Aspergillus fumigatus* allergens Asp f 1, Asp f3, Asp f 4, Asp f 6, Asp f 7 and Asp f 8; *Alternaria alternata* allergens Alt a 1 and Alt a 5; *Malassezia furfur* allergen Mal f 1, Mal f 5, Mal f 6, Mal f 7, Mal f 8, and Mal f 9; insects, such as *Blatella germanica* allergens Bla g 2, Bla g 4, and Bla g 5; *Apis mellifera* allergens Api m 2 and Api m 1; *Vespula vulgaris* allergen Ves v 5; *Vespula germanica* allergen Ves g 5; and *Polstes annularis* allergen Pol a 5; food, such as *Malus domestica* allergens Mal d 1 and Mal d 2; *Apium graveolens* allergend Api g 1 and Api g 1.0201; *Daucus carota* allergen Dau c 1; and *Arachis hypogaea* allergens Ara h 2 and Ara h 5 and the like.

iii. Bacterial Pathogen

Specific examples of bacterial pathogens include without limitation any one or more of (or any combination of) *Acinetobacter baumanii*, *Actinobacillus* sp., *Actinomycetes*, *Actinomyces* sp. (such as *Actinomyces israelii* and *Actinomyces naeslundii*), *Aeromonas* sp. (such as *Aeromonas hydrophila*, *Aeromonas veronii* biovar *sobria* (*Aeromonas sobria*), and *Aeromonas caviae*), *Anaplasma phagocytophilum*, *Alcaligenes xylosoxidans*, *Acinetobacter baumanii*, *Actinobacillus actinomycetemcomitans*, *Bacillus* sp. (such as *Bacillus anthracia*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melintensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtherias*, *Corynebacterium jeikeum* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium intracellulare*, *Mycobacterium avium*, *Mycobacterium bovis*, and *Mycobacterium marinum*), *Mycoplasm* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Plesiomonas shigelloides*. *Prevotella* sp., *Porphyromonas* sp., *Prevotella melaninogenica*, *Proteus* sp. (such as *Proteus vulgaris* and *Proteus mirabilis*), *Providencia* sp. (*such as Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus* saprophyticus), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio furnisii*), *Yersinia* sp. (such as *Yersinia enterocolitica*, *Yersinia pestis*, and *Yersinia pseudotuberculosis*) and *Xanthomonas maltophilia* among others.

Bacterial antigens suitable for use in the disclosed methods include proteins, polysaccharides, lipopolysaccharides, and outer membrane vesicles which may be isolated, purified or derived from a bacterium. In addition, bacterial antigens include bacterial lysates and inactivated bacteria formulations. Bacteria antigens can be produced by recombinant expression. Bacterial antigens preferably include epitopes which are exposed on the surface of the bacteria during at least one stage of its life cycle. Bacterial antigens include but are not limited to antigens derived from one or more of the bacteria set forth above as well as the specific antigens examples identified below.

*Neiserria gonorrhoeae* antigens include Por (or porin) protein, such as PorB (see, e.g., Zhu et al. (2004) *Vaccine* 22:660-669), a transferring binding protein, such as TbpA and TbpB (see, e.g., Price et al. (2004) *Infect. Immun.* 71(1):277-283), an opacity protein (such as Opa), a reduction-modifiable protein (Rmp), and outer membrane vesicle (OMV) preparations (see, e.g., Plante et al. (2000) *J. Infect. Dis.* 182:848-855); WO 99/24578; WO 99/36544; WO 99/57280; and WO 02/079243, all of which are incorporated by reference).

*Chlamydia trachomatis* antigens include antigens derived from serotypes A, B, Ba and C (agents of trachoma, a cause of blindness), serotypes Li, L3 (associated with Lymphogranuloma venereum), and serotypes, D-K. *Chlamydia trachomas* antigens also include antigens identified in WO 00/37494; WO 03/049762; WO 03/068811; and WO 05/002619 (all of which are incorporated by reference), including PepA (CT045), LcrE (CT089), Art (CT381), DnaK (CT396), CT398, OmpH-like (CT242), L7/L12 (CT316), OmcA (CT444), AtosS (CT467), CT547, Eno (CT587), HrtA (CT823), MurG (CT761), CT396 and CT761, and specific combinations of these antigens.

*Treponemapallidum* (Syphilis) antigens include TmpA antigen.

In some embodiments, a disclosed assay can be used to measure one or more antigens derived from a sexually transmitted disease (STD). Such antigens can provide for prophylactis or therapy for STDs such as chlamydia, genital herpes, hepatitis (such as HCV), genital warts, gonorrhea, syphilis and/or chancroid (see WO 00/15255, which is incorporated by reference). Antigens may be derived from one or more viral or bacterial STDs. Viral STD antigens for use in the invention may be derived from, for example, HIV, herpes simplex virus (HSV-I and HSV-2), human papillomavirus (HPV), and hepatitis (HCV). Bacterial STD antigens for use in the invention may be derived from, for example, *Neiserria gonorrhoeae*, *Chlamydia trachomatis*, *Treponemapallidum*, *Haemophilus ducreyi*, *E. coli*, and *Streptococcus agalactiae*.

iv. Fungal Pathogens

Exemplary fungal pathogens include one or more of *Trichophyton rubrum*, *T. mentagrophytes*, *Epidermophyton floccosum*, *Microsporum canis*, *Pityrosporum orbiculare* (*Malassezia furfur*), *Candida* sp. (such as *Candida albicans*), *Aspergillus* sp. (such as *Aspergillus fumigatus*, *Aspergillus flavus* and *Aspergillus clavatus*), *Cryptococcus* sp. (such as *Cryptococcus neoformans*, *Cryptococcus gattii*, *Cryptococcus laurentii* and *Cryptococcus albidus*), *Histoplasma* sp. (such as *Histoplasma capsulatum*), *Pneumocystis* sp. (such as *Pneumocystis jirovecii*), and *Stachybotrys* (such as *Stachybotrys chartarum*).

v. Parasites

Exemplary parasitic organisms include Malaria (*Plasmodium falciparum*, *P. vivax*, *P. malariae*), Schistosomes, Trypanosomes, Leishmania, Filarial nematodes, Trichomoniasis, Sarcosporidiasis, Taenia (*T. saginata*, *T. solium*), Leishmania, *Toxoplasma gondii*, Trichinelosis (*Trichinella spiralis*) or Coccidiosis (*Eimeria* species).

vi. Tumor Antigens

Exemplary tumor antigens (antigens produced by tumor cells that can stimulate tumor-specific T-cell immune responses) include one or more of the following RAGE-1, tyrosinase, MAGE-1, MAGE-2, NY-ESO-1, Melan-A/MART-1, glycoprotein (gp) 75, gp100, beta-catenin, preferentially expressed antigen of melanoma (PRAME), MUM-1, Wilms tumor (WT)-1, carcinoembryonic antigen (CEA), and PR-1. Additional tumor antigens are known in the art (for example see Novellino et al., *Cancer Immunol. Immunother.* 54(3):187-207, 2005) and are described below. Tumor antigens are also referred to as "cancer antigens." The tumor antigen can be any tumor-associated antigen, which are well known in the art and include, for example, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, macrophage colony stimulating factor, prostase, prostate-specific antigen (PSA), PAP, NY-ESO-1, LAGE-1a, p53, prostein, PSMA, Her2/neu, survivin and telomerase, prostate-carcinoma tumor antigen-1, MAGE, ELF2M, neutrophil elastase, ephrinB2, CD22, insulin growth factor (IGF)-I, IGF-II, IGF-I receptor and mesothelin. A list of selected tumor antigens and their associated tumors are shown below.

Exemplary Tumors and their Tumor Antigens

| Tumor | Tumor Associated Target Antigens |
|---|---|
| Acute myelogenous leukemia | Wilms tumor 1 (WT1), PRAME, PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | NY-ESO-1 |
| Malignant melanoma | MAGE, MART, Tyrosinase, PRAME GP100 |
| Breast cancer | WT1, Herceptin, epithelial tumor antigen (ETA) |
| Lung cancer | WT1 |
| Ovarian cancer | CA-125 |
| Prostate cancer | PSA |
| Pancreatic cancer | CA19-9, RCAS1 |
| Colon cancer | CEA |
| Cervical Cancer | SCC, CA125, CEA, Cytokeratins (TPA, TPS, Cyfra21-1) |
| Renal cell carcinoma (RCC) | Fibroblast growth factor 5 |
| Germ cell tumors | AFP |

In some embodiments, the assay is to detect an infection with a pathogen in an immunocompromised subject Immunocompromised subjects are more susceptible to opportunistic infections, for example viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressives, and those who are receiving chemotherapy for cancer. Immunocompromised individuals also includes subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also may be immunocompromised.

In other embodiments, the immunocompromised subject is infected with a lentivirus. Lentiviruses include, but are not limited to human immunodeficiency virus type 1 (HIV-1), human immunodeficiency virus type 2 (HIV-2), simian immunodeficiency virus agm (SIVagm), simian immunodeficiency virus mnd (SIVmnd), simian immunodeficiency virus syk (SIVsyk), simian immunodeficiency virus col (SIVcol), Visna-Maedi virus (VMV), bovine immunodeficiency virus (BIV), feline immunodeficiency virus (FIV), caprine arthritis-encephalitis virus (CAEV), and equine infectious anemia virus (EIAV). In some embodiments, the lentivirus is human immunodeficiency virus type 1 (HIV-1). In some embodiments, the lentivirus is human immunodeficiency virus type 2 (HIV-2). It is contemplated that pathogenic antigen can be an extract of the pathogen, or a synthetic protein or peptide fragment, or synthesized fragments of an antigenic particle of the pathogen with overlapping amino acid or nucleotide sequence.

In some embodiments, the method further comprises detecting a specific set of immune cells, such as B or T cells.

In one particular embodiment, the method includes assessing the uptake or API of B-cells. In this example, API is positively correlated with CD154 expression of the T and B-cells stimulated with the hepatitits virus or its fragments. An API of greater than 1 (hepatitits B/fragment/peptide uptake>uptake of reference antigen) indicates that a subject is at an increased risk of infection or the presence of Hepatitis B. Alternatively, if a threshold number of B-cells which take up hepatitis B is exceeded, then the person is at increased risk of hepatitis B.

In some examples, the plurality of biomarkers includes one or more markers for one or more of the pathogens listed above.

In further examples, a global assay is disclosed that allows diagnosing or predicting organ transplant rejection as described in detail in Section III in combination with diagnosing or predicting pathogen infection, such as viral or bacterial infection. For example, specific markers known to those of skill in the art are utilized to detect a particular viral and/or bacterial infection and at least CD27, IgM, IgA, IgG, IgD, CD5 and CD10 markers are utilized to diagnose or predict organ transplant rejection. It is contemplated that additional biomarkers can also be detected, such as additional memory cell markers (e.g., IgG), CD19, CD38 (plasma cell marker), and CD138 (plasma cell activation markers), CD154 (B-cell activation marker), CTLA4 (negative B-cell co-stimulator marker) and CD45 (pan-leukocyte/lymphocyte marker). In one example, any of the phenotypic markers disclosed herein are used alone or in combination.

In some embodiments, expression levels of the plurality of biomarkers are measured using flow cytometry or other methods known to those of skill in the art, including those described herein (see Section III and Examples).

The disclosure is further illustrated by the following non-limiting Examples.

EXAMPLES

Example 1

B-Cell Rejection Monitoring Assay

This example discloses a B-cell rejection monitoring assay for identifying recipients at risk for ACR and HR.

In these data sets, the rejection-prone recipient was labeled "a Rejector" and the rejection-free recipient "a Non-Rejector." Significantly higher API distinguished without overlap (100% sensitivity and specificity) children who had biopsy-proven rejection (Rejectors) after liver (LTx) or small bowel transplantation (SBTx), from those who were rejection-free (Non-Rejectors). (Table 1).

TABLE 1

| LTx | API (Median ± SEM) | SBTx | API (Median ± SEM) |
|---|---|---|---|
| NR n = 20 | 0.750 ± 0.048 | NR n = 18 | 0.555 ± 0.060 |
| R n = 15 | 1.794 ± 0.506 | R n = 11 | 1.781 ± 0.255 |
| p-value | 0.0030 | p-value | 0.0003 |

Additional data showed that various types of transplant recipients showed similar results. For example, similar results were observed in all B-cell compartments except the IgG+ compartment. These subsets, excluding IgG+ subsets are defined by the presence or absence of CD27, IgM, IgA, IgD, CD5, and CD10. The minimal numbers of markers include CD19 or CD20 to label a cell as B-cell, IgG and CD27 to call it a memory B-cell cell, and IgM or IgD to call it a naive B-cell. These studies provide support of the use of the API to diagnose ACR and HR and measure its risk.

API beared a significant positive correlation with inflammatory donor-specific B-cells, which expressed the inflammatory marker CD154 (allospecific CD154+TcM) (allospecific CD154+B-cells). These correlations were seen in either the liver or small bowel transplant recipient populations (Tables 2 and 3). Similar results were observed in all B-cell compartments except the IgG+ compartment. These subsets, excluding IgG+ subsets were defined by the presence or absence of CD27, IgM, IgA, IgD, CD5, and CD10.

TABLE 2

Correlations for donor antigen uptake of B-cells (API) with CD154+ and CTLA-4+ T-cytotoxic memory & B-cells in Liver transplant recipients.

| n = 14NR, 10R | CD19+B-cells |
|---|---|
| CD154+TcM (Spearman r) | 0.5600 |
| p: value | 0.0044 |
| CTLA4+TcM (Spearman r) | −0.5316 |
| p: value | 0.0090 |
| CD154+CD19 (Spearman r) | 0.6246 |
| p: value | 0.0019 |
| CTLA4+CD19 (Spearman r) | −0.6084 |
| p: value | 0.0027 |

TABLE 3

Correlations for donor antigen uptake of B-cells (API) with CD154+ and CTLA-4+ T-cytotoxic memory & B-cells in Small bowel transplant recipients.

| n = 17NR, 14R | CD19+B-cells |
|---|---|
| CD154+TcM (Spearman r) | 0.7855 |
| p: value | 0.00000017 |
| CTLA4+TcM (Spearman r) | −0.3931 |
| p: value | 0.0349 |
| CD154+CD19 (Spearman r) | 0.4347 |
| p: value | 0.0145 |

API had a significant negative correlation with antiinflammatory donor-specific T-cytotoxic memory cells which express the antiinflammatory marker CTLA4 (allospecific CTLA4+TcM). CTLA4+TcM were measured in a mixed leukocyte response (MLR). CTLA4+TcM could also be measured in the same study as the API, by extending the incubation from 40 minutes to 6-8 hours. These correlations were seen in either the liver or small bowel transplant recipient populations (Tables 2 and 3). Additional data showed that all types of transplant recipients would show similar results. Similar results were observed in all B-cell compartments except the IgG+ compartment. These subsets, excluding IgG+ subsets were defined by the presence or absence of CD27, IgM, IgA, IgD, CD5, and CD.

The IgG+ memory compartment of B-cells was less efficient at presenting donor antigen in the presence of humoral rejection, which might occur alone, or with Acute cellular rejection. In contrast, the API of naive B-cell compartments, such as IgD+ compartments, or the IgD+ CD27− compartments continued to show API>1 when ACR is present without HR.

These observations can be used to distinguish between HR and ACR. For example, the API of IgG+B-cells (memory) is expressed a ratio with the API of naive IgD+ B-cells. Effectively, this ratio is also a measure of donor antigen uptake by memory IgG+B-cells, relative to donor antigen uptake by the naive IgD+B-cells. The resulting memory:naive B-cell API ratio is <1 if humoral rejection is encountered alone or with ACR, and >1 if only ACR is present, without HR.

These studies support the use of the disclosed assay employing an API to diagnose ACR and HR as well as measure its risk.

Example 2

Organ Transplant Monitoring Assay

This example discloses an assay for identifying recipients at risk for ACR and HR in which it provides the following indications: (1) analysis of B-cells which take up donor antigen; (2) characterization of the B-cell alloresponse (e.g., whether inflammatory or anti-inflammatory); and characterization of the T-cytotoxic memory cell alloresponse (e.g., whether inflammatory or anti-inflammatory).

The API of B-cells, it's naive and memory compartments, and the resulting production of CD154 and CTLA4 in T- and B-cells, which are described in Example 1 are all combined into a single 6-8 hour test, in which dye-labeled donor and third-party antigen act as stimulators. Polychromatic flow cytometry is used to measure B-cell antigen presentation, and B- and T-cell inflammatory or anti-inflammatory alloresponse simultaneously. This combined assay provides a comprehensive analysis of B-cells which take up donor antigen, the character of the B-cell alloresponse, whether inflammatory or anti-inflammatory, and the alloresponse of T-cytotoxic memory cells, whether inflammatory or anti-inflammatory.

Example 3

B-Cell Antigen Presentation Assay

The example provides a B-cell antigen-presentation assay for detecting risk of rejection in subjects with a transplanted organ.

Assay System: Lymphocytes obtained from a transplant recipient were mixed with donor antigen or with third-party antigen. Third-party antigen included antigen from an individual who is antigenically dissimilar to the recipient or the donor. Antigenic similarity or dissimilarity was determined at the HLA loci. These histocompatibility loci included the major class I (e.g., HLA-A, -B and -C) and class II (e.g. HLA-DR, -DP, -DQ, -DOA, -DOB and -DM) loci. If actual donor antigen was not available, antigen from normal human subjects which was matched with actual donor at the HLA loci was used. The ratio of donor antigen to third-party antigen uptake and presentation was the API. If the donor antigen presentation exceeded that due to third-party, the API was usually >1 and the individual was at increased risk of rejection. If the donor antigen presentation was exceeded by the third-party antigen, the API is usually <1 and the individual is at decreased risk of rejection. As shown in FIG. 1, in the rejector (upper panels) 23.6% recipient B-cells presented donor antigen (middle upper panel), compared with 4.8% recipient B-cells which presented third-party antigen (right upper panel) for an API of 4.91. In the non-rejector (lower panels), 35.9% of recipient B-cells presented third-party antigen (lower right panel), but only 13.3% presented donor antigen (lower middle panel). The API is 0.037 in this non-rejector.

The uptake and presentation of antigen was measured by placing donor or third-party antigen in contact with either purified B-cells, or peripheral blood leukocytes (PBL) from the recipient. Thereafter, imaging techniques (such as flow cytometry, or a variety of microscopic techniques, e.g., confocal microscopy) were used to measure antigen which has been taken up by the B-cell.

Tables 4-7 summarize differences in the API between rejectors and non-rejectors for some of the common subsets of B-cells in children who had received liver (Table 4) or intestine transplantation (Table 5), or the combined liver or intestine transplant population (Table 6) and adult renal transplant recipients (Table 7). The B-cell was identified with the marker CD19. B-cell subsets were labeled with CD27, a memory marker, and IgG+ another marker of B-cell memory. One measurement was included per subject, made either in proximity to biopsy-proven rejection (rejector status) or an established rejection-free (non-rejector status). Within the liver or the intestine transplant cohort, some subjects had only received a single measurement, and others had been monitored serially before transplantation, and at days 1-60 and 61-200 after transplantation. The single measurement from serially monitored liver or intestine patients which has been included in Tables 4-6 was one made during days 1-60 after transplantation.

TABLE 7

Differences in median ± SEM antigen presentation index (API) of CD19+B-cells between non-rejectors and rejectors after renal transplantation.

| Combined | CD19+API |
|---|---|
| Non-rejectors (n = 10) | 0.624 ± 0.14 |
| Rejectors (n = 7) | 1.49 ± 3.6 |
| p-value (one tail) | 0.039 |

Assay performance was then evaluated with sensitivity and specificity testing using the illustrative dataset summarized in Tables 4-6 for children with liver (Table 4) or intestine transplantation (Table 5) or the combined cohort of liver or intestinal transplant recipients (Table 6). The sensitivity was the proportion of rejectors with an API exceeding the rejection-risk threshold. The specificity was the proportion of non-rejectors with an API below the rejection-risk threshold.

Rejection-risk thresholds were identified and tested for each subject population using logistic regression and screening-replication testing. Liver recipients shown in Table 4 were divided into a screening cohort of 43 recipients in whom a single (cross-sectional) API measurement was available in proximity to biopsy-proven rejection or an established non-rejector course. The sensitivity and specificity of this threshold was then confirmed in 17 remaining

TABLE 4

Differences in median ± SEM antigen presentation index (API) between non-rejectors and rejectors after liver transplantation. (Legend: B-cell = CD19+, Memory B-cell = CD19+CD27+, naïve B-cell = CD19+CD27−, Memory IgG+B-cell = CD19+IgG+, Naïve IgG−B-cell = CD19+IgG−.).

| Outcome | CD19+ | CD19+CD27+ | CD19+CD27− | CD19+IgG+ | CD19+IgG− |
|---|---|---|---|---|---|
| Non-rejectors (n = 34) | 0.512 ± 0.057 | 0.589 ± 0.083 | 0.433 ± 0.177 | 0.843 ± 0.108 | 0.738 ± 0.305 |
| Rejectors (n = 26) | 1.794 ± 0.237 | 1.411 ± 0.243 | 1.738 ± 0.710 | 1.303 ± 0.151 | 1.703 ± 0.317 |
| p-value | 3.12E−07 | 0.0006 | 0.0015 | 0.011 | 0.005 |

TABLE 5

Differences in median ± SEM antigen presentation index (API) between non-rejectors and rejectors after intestine transplantation. (Legend: see Table 4).

| Outcome | CD19+ | CD19+CD27+ | CD19+CD27− | CD19+IgG+ | CD19+IgG− |
|---|---|---|---|---|---|
| Non-rejectors (n = 34) | 0.601 ± 0.048 | 0.660 ± 0.072 | 0.546 ± 0.097 | 0.620 ± 0.133 | 0.553 ± 0.067 |
| Rejectors (n = 22) | 1.94 ± 0.427 | 1.386 ± 0.218 | 2.586 ± 0.957 | 0.968 ± 0.396 | 2.333 ± 0.980 |
| p-value | 4.38E−05 | 0.0001 | 0.001 | 0.042 | 0.014 |

TABLE 6

Differences in median ± SEM antigen presentation index (API) between non-rejectors and rejectors in the combined population of liver or intestine transplant recipients shown in Tables 4 and 5. (Legend: see Table 4).

| Combined | CD19+ | CD19+CD27+ | CD19+CD27− | CD19+IgG+ | CD19+IgG− |
|---|---|---|---|---|---|
| Non-rejectors (n = 68) | 0.543 ± 0.037 | 0.625 ± 0.054 | 0.477 ± 0.100 | 0.677 ± 0.088 | 0.608 ± 0.141 |
| Rejectors (n = 48) | 1.79 ± 0.235 | 1.411 ± 0.164 | 2.058 ± 0.578 | 1.208 ± 0.197 | 1.898 ± 0.470 |
| p-value | 2.86E−10 | 2.21E−07 | 4.1E−06 | 0.002 | 0.0002 | liver recipients called a replication cohort, in whom API measurements were made longitudinally, before transplantation and at 1-60 and 61-200 days after liver transplantation. For replication purposes, the sensitivity and specificity of the rejection-risk threshold identified in the screening cohort were re-tested using pre-transplant and 1-60-day API data.

In a manner similar to liver recipients, intestine transplant patients summarized in Table 5 consisted of 45 cross-sectionally monitored recipients who made up the screening cohort, and the remaining 11 longitudinally monitored recipients, who made up the replication cohort.

Table 8 below shows the rejection-risk thresholds for B-cell antigen presentation (CD19+cells) derived from liver recipients, intestine recipients, and the combined population which make up the respective screening (cross-sectional) cohorts. The thresholds at or above which rejector status was predicted for the liver, intestine or the combined screening cohorts were 1.115, 1.115 and 1.108, respectively. The sensitivity and specificity of these thresholds were confirmed in the respective replication cohorts, for two of three longitudinal API measurements, the pre-transplant API and the post-transplant API at 1-60 days. For each sensitivity value, the numbers of rejectors identified correctly, for e.g. 11 of 13 liver recipients with API≥1.115 are shown in the Table. Similarly, the numbers of non-rejectors identified as having API below the rejection-risk threshold are also shown.

TABLE 8

Summary of sensitivity and specificity testing of the rejection-risk threshold API in children with liver or intestine transplantation or the combined population

| | | threshold API | Sensitivity | Specificity |
|---|---|---|---|---|
| Screening cohort | | | | |
| Cross sectional API | Liver | ≥1.115 | 84.6% (11 of 13) | 96.7% (29 of 30) |
| | Intestine | ≥1.115 | 100% (15 of 15) | 96.7% (29 of 30) |
| | Combined | ≥1.108 | 92.9% (26 of 28) | 96.7% (58 of 60) |
| Replication cohort | | | | |
| Pre-transplant API | Liver | ≥1.115 | 87.5% (7 of 8) | 100% (2 of 2) |
| | Intestine | ≥1.115 | 100% (3 of 3) | 100% (3 of 3) |
| | Combined | ≥1.108 | 90.9% (10 of 11) | 100% (5 of 5) |
| Post-transplant API at days 1-60 | Liver | ≥1.115 | 100% (13 of 13) | 100% (4 of 4) |
| | Intestine | ≥1.115 | 100% ((7 of 7) | 100% (4 of 4) |
| | Combined | ≥1.108 | 100% (20 of 20) | 100% (8 of 8) |

Figure 2:
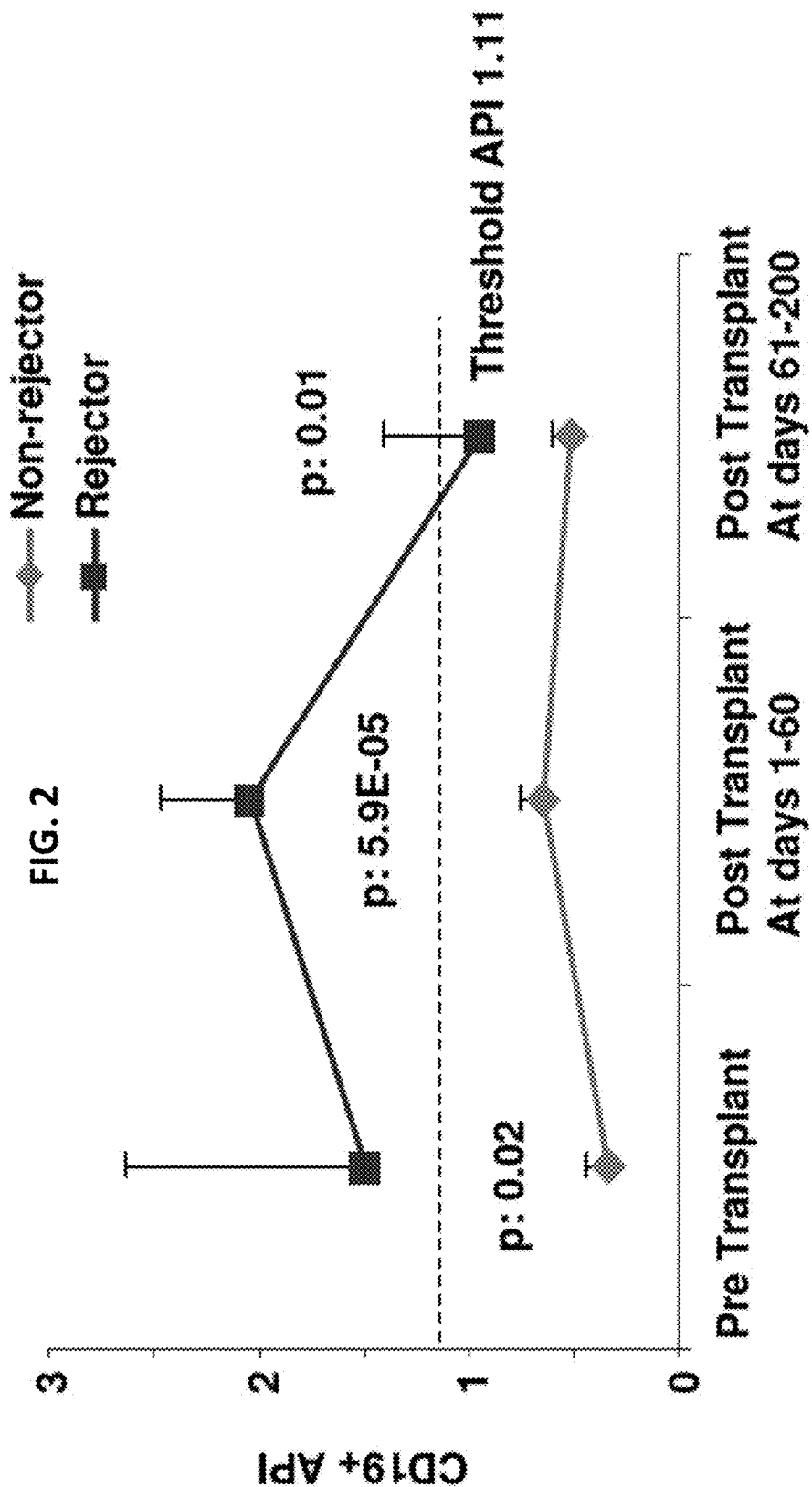
FIG. 2 is a graph of the API from 28 children with liver or intestine transplantation at three different time points. The majority of non-rejectors (bottom panel) remained below the rejection-risk threshold API of <1.11 at all three timepoints. The majority of rejectors (black lines, top panel) were at or above the rejection-risk threshold IR of 1.11 before and during the first 1-60-days after transplantation, but below this threshold during the 61-200-day period after transplantation. Error bars represent the standard error of the mean.

The dynamic nature of the API in the same individual was illustrated for 28 children who had been monitored serially, before transplantation and at days 1-60 and 61-200 after liver or intestine transplantation (FIG. 2). These results show that rejectors (who experience rejection within the first 60 days after transplantation) show increased risk of rejection in the form of an API at or above the rejection-risk threshold API≥1.11 before transplantation. Rejectors also shows increased risk of rejection during the rejection-prone period of 1-60 days, but show reduced rejection risk characterized by an API<1.11 during the later part of the follow-up. In contrast, most non-rejectors are likely to show reduced risk of rejection characterized by an API<1.11 before transplantation which is likely to persist through the post-transplant course.

A benefit of the B-cell antigen presenting assay is its ability to utilize a "surrogate donor" antigen instead of actual donor antigen. Actual donor antigen usually consists of peripheral blood leukocytes or spleen cells called splenocytes which are obtained from the donor and consumed during the tissue typing tests required at each of many centers that receive the various organs from a donor for transplantation. Lifelong testing using actual donor cells is therefore not possible. An illustrative study summarized in FIG. 3 shows that whether actual donor antigen was used, or surrogate donor antigen is used, the assignment of rejector or rejector status does not change if a rejection-risk threshold of 1.115 is used. Four non-rejectors and 2 rejectors have been tested simultaneously using actual donor and surrogate donor stimulators in this study. For each recipient, the same third-party stimulator was used to calculate the API with either actual donor or surrogate donor stimulator.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

We claim:

1. A method, comprising:
   obtaining antigen presenting cells (APCs);
   contacting a first sample of the obtained APCs with an antigen from an infectious pathogen under conditions sufficient to induce uptake of the donor antigen;
   contacting a second sample of the obtained APCs with a reference antigen under conditions sufficient to induce uptake of the reference antigen; and measuring uptake of the antigen from the infectious pathogen in the first sample and uptake of the reference antigen in the second sample by flow cytometry; and
   detecting a plurality of biomarkers following contacting of the first sample with the antigen from the infectious pathogen and the second sample with the reference antigen, and comparing the plurality of biomarkers detected in the first sample following treatment with the antigen from the infectious pathogen to the plurality of biomarkers detected in the second sample.

2. The method of claim 1, wherein the first sample and the second sample are peripheral blood lymphocytes or peripheral blood leukocytes.

3. The method of claim 1, further comprising expressing uptake of the antigen from the infectious pathogen relative to uptake of the reference antigen following measuring uptake of the antigen from the infectious pathogen in the first sample and uptake of the reference antigen in the second sample by flow cytometry.

4. The method of claim 1, wherein the method is used to evidence effectiveness of a therapeutic regimen.

5. The method of claim 1, wherein the infectious pathogen is a virus, bacteria or a fungus.

6. The method of claim 1, wherein the reference antigen is a non-pathogenic antigen from a different pathogen.

7. The method of claim 1, wherein the antigen from the infectious pathogen or the reference antigen comprises cells, cell lysate, an antigenic peptide, an antigenic peptide labeled with a detectable label, such as a fluorochrome, or a combination thereof.

8. The method of claim 1, wherein the antigen from the infectious pathogen or the reference antigen are labeled with a fluorescent marker.

9. The method of claim 8, wherein the fluorescent marker is carboxyflouresciensuccinimyldiester.

10. A method, comprising:
  obtaining antigen presenting cells (APCs);
  labeling an antigen from an infectious pathogen and a reference antigen with a fluorescent molecule;
  contacting a first sample of the obtained APCs with fluorescently labeled antigen from the pathogen under conditions sufficient to induce uptake of the fluorescently labeled antigen from the infectious pathogen;
  contacting a second sample of the obtained APCs with fluorescently labeled reference antigen under conditions sufficient to induce uptake of the fluorescently labeled reference antigen; and
  measuring uptake of the fluorescently labeled antigen from the infectious pathogen in the first sample and uptake of the fluorescently labeled reference antigen in the second sample by flow cytometry;
  expressing uptake of the antigen from the infectious pathogen relative to uptake of the reference antigen;
  detecting a plurality of biomarkers following contacting of the first sample with the antigen from the infectious pathogen and the second sample with the reference antigen, wherein the plurality of biomarkers includes at least CD24 and CD38; and
  comparing the plurality of biomarkers detected in the first sample following treatment with the antigen from the infectious pathogen to the plurality of biomarkers detected in the second sample.

11. The method of claim 10, wherein the antigen from the infectious pathogen comprises cells, a cell lysate, an antigenic peptide.

12. The method of claim 10, wherein the pathogen is a bacteria, a virus or a fungus.

13. The method of claim 10, wherein the reference antigen is a non-pathogenic antigen from a different pathogen.

14. The method of claim 10, wherein the fluorescent molecule is carboxyflouresciensuccinimyldiester.

15. The method of claim 1, wherein the APCs are B cells, and wherein the plurality of biomarkers comprises CD24 and CD38.

16. The method of claim 15, wherein the plurality of biomarkers comprises immunoglobulin (Ig) D.

17. The method of claim 15, wherein the plurality of markers comprises CD27.

18. The method of claim 15, wherein the plurality of markers comprises CD19.

19. The method of claim 10, wherein the APCs are B cells, and wherein the plurality of biomarkers comprises CD24 and CD38.

20. The method of claim 19, wherein the plurality of biomarkers comprises immunoglobulin (Ig) D.

21. The method of claim 19, wherein the plurality of markers comprises CD27.

22. The method of claim 19, wherein the plurality of markers comprises CD19.

* * * * *